United States Patent [19]
Pepys et al.

[11] Patent Number: 6,126,918
[45] Date of Patent: Oct. 3, 2000

[54] SCREENING ASSAYS TO IDENTIFY THERAPEUTIC AGENTS FOR AMYLOIDOSIS

[75] Inventors: Mark B. Pepys; Thomas L. Blundell, both of London, United Kingdom

[73] Assignee: Imperial College Innovations Limited, London, United Kingdom

[21] Appl. No.: 08/596,184

[22] PCT Filed: Aug. 17, 1994

[86] PCT No.: PCT/GB94/01802

§ 371 Date: Aug. 22, 1996

§ 102(e) Date: Aug. 22, 1996

[87] PCT Pub. No.: WO95/05394

PCT Pub. Date: Feb. 23, 1995

[30]     Foreign Application Priority Data

Aug. 17, 1993 [GB] United Kingdom .................... 9317120

[51] Int. Cl.$^7$ ........................... G01N 33/53; A61K 49/00
[52] U.S. Cl. ............................. 424/9.1; 424/9.2; 435/7.8; 436/503
[58] Field of Search .................................. 424/130.1, 9.1, 424/9.2; 436/503; 435/7.8

[56]             References Cited

U.S. PATENT DOCUMENTS 5,221,628   6/1993   Anderson et al. .

OTHER PUBLICATIONS

Alper, "Drug Discovery on the Assembly Line," *Science*, 264:1399–1401, Jun. 1994.
Breathnach et al., "Amyloid P Component is Located on Elastic Fibre Microfibrils in Normal Human Tissue," *Nature*, 293:652–654, Oct. 1981.
Butler et al., "Pentraxin–Chromatin Interactions: Serum Amyloid P Component Specifically Displaces H1–Type Histones and Solubilizes Native Long Chromatin," *J. Exp. Med.*, 172:13–18, Jul. 1990.
De Beer et al., "Fibronectin and C4–Binding Protein are Selectively Bound by Aggregated Amyloid P Component," *J. Exp. Med.*, 154:1134–1149, Oct. 1981.
Dyck et al., "Amyloid P–Component in Human Glomerular Basement Membrane," In: *The Lancet*, vol. 2, 606–609, Jul.–Dec. 1980.
Dyck et al., "Amyloid P–Component is a Constituent of Normal Human Glomerular Basement Membrane," *J. Exp. Med.*, 152:1162–1174, Nov. 1980.
Einsphar, "The Crystal Structure of Pea Lectin at 3.0–Å Resolution," *J. Biol. Chem.*, 261:16518–16527, Dec. 1986.
Emsley et al., "Structure of Pentameric Human Serum Amyloid P Component," *Nature*, 367:338–345, Jan. 1994.
Hawkins et al., "Evaluation of Systemic Amyloidosis by Scintigraphy with $^{123}$I–Labeled Serum Amyloid P Component," *New Eng. J. Med.*, 323(8):508–513, Aug. 1990.
Hamazaki, "$Ca^{2+}$–Mediated Association of Human Serum Amyloid P Component with Heparan Sulfate and Dermatan Sulfate," *J. Biol. Chem.*, 262(4):1456–1460, Feb. 1987.
Hawkins et al., "Scintigraphic Quantification and Serial Monitoring of Human Visceral Amyloid Deposits Provide Evidence for Turnover and Regression," *Quarterly Journal of Medicine*, 86:365–374, 1993.
Hawkins et al., "Serum Amyloid P Component Scintigraphy and Turnover Studies for Diagnosis and Quantitative Monitoring of AA Amyloidosis in Juvenile Rheumatoid Arthritis," *Arthritis and Rheumatism*, 36(6):842–851, Jun. 1993.
Hawkins et al., "Regression of AL Amyloidosis and Prolonged Survival Following Cardiac Transplantation and Chemotherapy," In: Proceedings of VII International Symposium on Amyloidosis, Parthenon Publishing, Pearl River, NY, 1993.
Hawkins et al., "Natural History and Regression of Amyloidosis," In: Proceedings of VII International Symposium on Amyloidosis, Parthenon Publishing, Pearl River, NY, 1993.
Hind et al., "Specific Chemical Dissociation of Fibrillar and Non–Fibrillar Components of Amyloid Deposits", *The Lancet*, vol. 2, 376–378, Aug. 1984.
Hind et al., "Binding Specificity of Serum Amyloid P Component for the pyruvate Acetal of Galactose," *J. Exp. Med.*, 159:1058–1069, Apr. 1984.
Holmgren et al., "Clinical Improvement and Amyloid Regression After Liver Transplantation in Hereditary Transthyretin Amyloidosis," *The Lancet*, 341:1113–1116, May, 1993.
O'Hara et al., "Crystallizations of Human Serum Amyloid P Component (SAP)," *Journal of Crystal Growth* 90:209–212, 1988.
Pepys et al., "Analogues in Other Mammals and in Fish of Human Plasma Proteins, C–Reactive Protein and Amyloid P Component," *Nature*, 273:168–170, May 1978.
Pepys and Baltz, "Acute Phase Proteins with Special Reference to C–Reactive Protein and Related Proteins (Pentaxins) and Serum Amyloid A Protein," *Advances in Immunology*, 34:141–212, 1983.
Pepys and Butler, "Serum Amyloid P Component is the Major Calcium–Dependent Specific DNA Binding Protein of the Serum," *Biochemical and Biophysical Research Communications*, 148(1):308–313, Oct. 1987.
Pepys et al., "Specific Molecular Targeting of Amyloid Deposits in Man," *Medical Research Council News*, No. 42, pp. 8–9, Mar. 1989.

(List continued on next page.)

*Primary Examiner*—Patricia A. Duffy
*Attorney, Agent, or Firm*—Williams, Morgan & Amerson

[57]             ABSTRACT

Therapeutical and diagnostic agents for amyloidosis comprise molecules that inhibit the binding of serum amyloid P component to amyloid fibrils or analogues or homologues of the amyloid binding site on serum amyloid P component. The resolution of the complete three dimensional structure of serum amyloid P component enables inhibitors, binding site analogues and homologues to be designed by computer-aided molecular modelling.

26 Claims, 15 Drawing Sheets

OTHER PUBLICATIONS

Potempa et al., "Effect of Divalent Metal Ions and pH Upon the Binding Reactivity of Human Serum Amyloid P Component, a C–Reactive Protein Homologue, for Zymosan," *J. Biol. Chem.*, 260(22):12142–12147, Oct. 1985.

Rufino and Blundell, "Structure–Based Identification and Clustering of Protein Families and Superfamilies," *Journal of Computer–Aided Molecular Design*, 8:5–27, 1994.

Swanson et al., "Human Serum Amyloid P–Component (SAP) Selectively Binds to Immobilized or Bound Forms of C–Reactive Protein (CRP)," *Biochimica et Biophysica Acta*, 1160:309–316, 1992.

Wood et al., "A Pentameric Form of Human Serum Amyloid P Component," *J. Mol. Biol.*, 202:169–173, 1988.

International Search Report, mailed Feb. 12, 1994.

6,126,918

SCREENING ASSAYS TO IDENTIFY THERAPEUTIC AGENTS FOR AMYLOIDOSIS

The present application is a nationalization of International Application No. PCT/GB 94/01802, filed Aug. 17, 1994; which has a priority date of Aug. 17, 1993.

1. Field of the Invention

The present invention relates to therapeutic and diagnostic agents for amyloidosis. The invention also relates to the three-dimensional structure of human serum amyloid P component and to the use of that structure in the production of therapeutic and diagnostic agents.

2. Description of the Related Art

Amyloidosis is the abnormal deposit of autologous proteins as insoluble fibrils in tissues. There are many different forms, each associated with a different fibril protein. Although microscopic amyloid deposition is always present in the elderly, and rarely causes clinical problems, more substantial amyloidosis, especially in the vital organs, is associated with progressive, untreatable and usually fatal disease. The most common disorders associated with amyloidosis are Alzheimer's disease and maturity onset diabetes mellitus. Other forms of acquired and hereditary amyloidosis are rarer but cause serious morbidity and are generally fatal.

Serum amyloid P component (SAP), a normal human plasma protein, is a universal constituent of amyloid deposits in all forms of amyloidosis, including the cerebral amyloid of Alzheimer's disease [1], as a result of its specific calcium-dependent binding affinity for amyloid fibrils [2]. The role, if any, of SAP in the pathogenesis or persistence of amyloid in vivo is not known and amyloid fibrils can be generated in vitro from suitable precursor proteins in the absence of SAP. However, SAP in amyloid is identical to its normal circulating form, it is not catabolised in the deposits in contrast to its normal rapid uptake from the circulation and catabolism in hepatocytes, and it is itself highly resistant to proteolytic degradation.

Human serum amyloid P component is a decameric plasma glycoprotein composed of identical subunits non-covalently associated in two pentameric rings interacting face-to-face. Although SAP is not required for amyloid fibrillogenesis in vitro, it may protect the fibrils from degradation in vivo [3]. SAP is also the major DNA and chromatin binding protein of plasma [4,5] and other autologous ligands for SAP include fibronectin, C4-binding protein [6] and glycosamino-lycans [7]; SAP is also a normal tissue matrix constituent associated with elastic fibres [8] and the glomerular basement membrane [9]. Finally, SAP is a calcium-dependent lectin, the best characterised ligand of which is the 4,6-cyclic pyruvate acetal of β-D-galactose (MOβDG) [10].

Human SAP shows no polymorphism or heterogeneity of its protein or its glycan [11] and no individual deficient in SAP has yet been described, suggesting that the molecule has important functions. Furthermore, SAP and C-reactive protein (CRP), the classical acute phase protein with which it shares over 50% sequence identity, belong to the pentraxin family of plasma proteins which have been stably conserved throughout vertebrate evolution [12,13]. The structure and structure-function relationships of SAP are thus of considerable fundamental interest, in addition to their clinical importance which arises from the invaluable new information provided by use of radio-labelled SAP as a specific quantitative in vivo tracer for amyloid deposits [14]. The speed and specificity with which SAP from the circulation localises to amyloid deposits and its prolonged retention there make SAP an interesting targeting agent. As indicated above, however, in spite of various observations and speculations, the role if any of SAP in the pathogenesis and persistence of amyloid in vivo was not known.

SUMMARY OF THE INVENTION

The present invention is based on our complete resolution of the three-dimensional structure of SAP, and also on our demonstration that the binding of SAP in vitro to amyloid fibrils at a specific binding site protects those fibrils from proteolytic degradation in the presence of proteinases. Results obtained on amyloid development in vivo confirms the in vitro results. We believe, therefore, that SAP is needed for amyloidogenesis, possibly to protect newly formed fibrils from proteolysis. Inhibition or reversal of the binding of SAP to fibrils will expose those fibrils to destruction, for example, by macrophages and/or released proteinases. Inhibition or reversal of binding of SAP to amyloid fibrils (either newly synthesised fibrils or established fibrils) may therefore be used for the treatment and/or prophylaxis of amyloidosis, including Alzheimer's disease.

Accordingly, the present invention provides a molecule, especially a physiologically tolerable molecule, that inhibits the binding of serum amyloid P component to amyloid fibrils. The inhibition may be competitive or non-competitive, and may be reversible or irreversible. The mechanism of inhibition may be via direct inhibition with the ligand binding site of SAP or it may be allosteric. A molecule of the invention may be regarded either as an SAP inhibitor or as an SAP ligand. The term "inhibition of binding of SAP to amyloid fibrils" as used herein includes both the prevention of such binding and also the reversal of binding that has already occurred.

The present invention also provides an analogue or homologue of the binding site for amyloid fibrils on SAP and further provides a low molecular weight polypeptide or other molecule having a high affinity for amyloid fibrils. Such a substance (binding site analogue or homologue or high affinity molecule) should preferably have greater affinity for amyloid fibrils than does SAP. The use of such a binding site analogue or homologue or molecule having a high affinity for amyloid fibrils, particularly a substance that has a higher affinity for amyloid fibrils than does SAP itself will inhibit, prevent or reverse the binding of SAP to amyloid fibrils, for example, it will displace SAP from the fibrils. Provided the binding site analogue or homologue or molecule having high affinity for amyloid fibrils does not have proteinase resistance and/or does not confer protection against proteinase activity to the amylo.id fibrils (at least not to the same extent as does SAP), such substances may be used in the treatment or prophylaxis of amyloidosis.

Any method of detecting or determining inhibition of binding of one molecule to another molecule may be used to identify a molecule that inhibits binding of SAP to amyloid fibrils; a detailed Protocol of one such test is given in Example 1. Further tests include the effects on the inhibition by SAP of proteolytic digestion of amyloid fibrils obtained ex vivo or produced in vitro from synthetic β-protein. Such methods are described generally below and in detail in Example 2.

Such tests may be also used to determine the ability of a binding site analogue or homologue or of a high affinity substance to bind to amyloid fibrils, for example, by investigating the binding to amyloid fibrils of a radio-labelled candidate molecule in an analogue of the protocol given in Example 1 below, for assessing potential inhibitors. (The term "high affinity substance" is used to denote a low molecular weight polypeptide or other molecule having a high affinity for amyloid fibrils, preferably an affinity greater than that of SAP. "High affinity" generally denotes binding in the micromolar to nanomolar range.)

The invention also provides a pharmaceutical preparation which comprises a physiologically tolerable molecule of the invention, for example, an inhibitor, binding site analogue or homologue or high affinity substance, in admixture or conjunction with a pharmaceutically suitable carrier. The invention also provides such a molecule of the present invention for use as a medicament, especially for the treatment or prophylaxis of amyloidosis, and further provides the use of such a molecule for the manufacture of a medicament for the treatment or prophylaxis of amyloidosis, especially Alzheimer's disease.

As described below, the molecules of the invention, especially the binding site analogues and homologues and high affinity substances, may also be used for in vivo diagnostic imaging.

Candidate molecules for testing for inhibition of SAP binding to amyloid fibrils may be selected at random, or may be chosen or designed on the basis of similarity to compounds known to inhibit such binding, for example, MOβDG and phosphoethanolamine (PE). However, such a screening strategy inevitably has a low success rate; it is time-consuming and the results are unpredictable.

Our resolution of the three-dimensional structure SAP, including the structure and topology of various binding sites, including the putative amyloid binding site, enables compounds to be designed specifically, and so leads to a much higher success rate. The design of candidate inhibitors of amyloid fibril binding and of binding site analogues and homologues and high affinity substances may be carried out by any of the well-known methods of molecular modelling, for example, computer-aided molecular design (CAMD). Candidate molecules are then synthesised and tested by an in vitro assay for their ability to inhibit the binding of SAP to amyloid fibrils or to function as a binding site analogue or homologue or high affinity substance. If desired, a molecule synthesised on the basis of a CAMD can be modified, for example, chemically and the modified molecules screened for their binding ability using the tests described herein.

A molecule of the present invention may belong to any class of chemical provided it achieves the desired effect. For example, an inhibitor or high affinity molecule may be a polypeptide or peptide, an oligonucleotide, an oligosaccharide or any type of organic chemical. Even small molecules may be effective, c.f., phosphoethanolamine. A binding site analogue or homologue is generally a polypeptide. A molecule of the invention may be a naturally-occurring substance or may be derived from such a substance. A molecule of the present invention may be synthesised de novo, for example, by combinatorial chemistry or may be designed by molecular modelling.

The present invention therefore includes all novel molecules that inhibit the binding of SAP to amyloid fibrils or that are binding site analogues or homologues or that are high affinity substances, including for example, those obtained by molecular modelling and synthesis and those obtained by combinatorial chemistry.

The invention also includes the use of substances known per se, for example, for other purposes, in the prevention, reversal or inhibition of the binding of SAP to amyloid fibrils and hence in the treatment of amyloidosis, especially Alzheimer's disease and maturity onset diabetes mellitus. The invention further provides use of a molecule according to the present invention for the manufacture of a medicament for the prevention, reversal or inhibition of the binding of SAP to amyloid fibrils and hence for the manufacture of a medicament for the treatment or prophylaxis of amyloidosis, especially Alzheimer's disease and maturity onset diabetes mellitus.

For use in treatment or diagnosis in vivo a molecule of the present invention must be physiologically tolerable. A molecule that is not physiologically tolerable may be used in in vitro investigations of amyloidosis and its treatment.

It will be appreciated that a candidate molecule will be synthesised by a method appropriate for that type of molecule, for example, an organic chemical compound will be synthesised chemically; a protein or peptide may be obtained by synthesis from amino acids or by recombinant DNA technology.

As described briefly above, we have now convincingly demonstrated that SAP does indeed protect amyloid fibrils from digestion by proteinases and does so exclusively by binding to them rather than acting as an enzyme inhibitor. We have also shown that SAP binds to amyloid fibrils at the MOβDG binding site.

Amyloid fibrils of AA (reactive systemic), AL (monoclonal IgG light chain) and apoAI (apoprotein AI) type were isolated from the organs of patients dying from amyloidosis and were shown to be digested during incubation at 37° C. in vitro with the proteolytic enzymes, for example, pronase, trypsin and chymotrypsin. Digestion was monitored by analysis of the incubation mixtures in reduced SDS-PAGE and also by release of trichloroacetic acid (TCA)-soluble radioactivity when the fibrils had been oxidatively labelled with $^{125}$I. Incubation of such labelled fibrils with cultured monocyte-derived macrophages also led to digestion.

In all cases addition of highly purified SAP to the incubation mixtures, under conditions in which the SAP could bind to the fibrils, resulted in greatly reduced fibril digestion. This inhibition was dose and time-dependent and was not observed when other proteins, C-reactive protein (CRP) and human serum albumin, were added as controls in place of SAP. CRP is a particularly good control since its structure is extremely similar to that of SAP, and it shares the same remarkable proteinase resistance, but it does not bind to amyloid fibrils and had no effect on their digestion. When albumin was used as the control protein both it and the fibrils were completely digested by the proteinases.

However, we found that the protective effect of SAP was completely abrogated when MOβDG was included in the incubation mixtures. This low molecular weight specific ligand of SAP competitively inhibits binding of SAP to amyloid fibrils, as we have previously reported [3,10]. The presence of SAP in the incubation mixtures thus had no effect on proteolysis of the fibrils when it was prevented from binding to them by the presence of MOβD.

Since SAP binds to all types of amyloid fibrils in vivo we conclude that SAP is also likely to prevent the fibrils from being degraded in vivo by cells, such as macrophages, and/or released proteinases. Agents capable of inhibiting or reversing the binding of SAP to amyloid fibrils in vivo will therefore facilitate and accelerate digestion and removal of the fibrils, leading to clearance of amyloid deposits and remission of their clinical and pathological effects.

We have now also demonstrated that SAP undergoes typical calcium-dependent binding to amyloid fibrils produced in vitro from synthetic β-protein. β-protein is the subunit of the amyloid fibrils which are deposited in the brain and cerebral blood vessels in Alzheimer's disease (AD). Evidence linking β-protein amyloidosis in the brain to the pathogenesis of AD is now very powerful [54]. We have now shown that SAP protected the β-protein amyloid fibrils from proteolysis in precisely the same fashion as it protected the ex vivo fibrils, and the protection was completely abrogated by MOβDG. Furthermore, exactly the same results have been obtained using ex vivo amyloid fibrils isolated from the brain of a patient with Alzheimer's disease. A drug capable of exercising the same effect in vivo within the brain will therefore confer great therapeutic benefit in AD.

In a separate line of investigation we have studied the capacity of mice deprived of SAP to develop AA amyloidosis in an accelerated model of amyloidogenesis. Amyloid was induced rapidly by intravenous injection of an extract of amyloidotic spleen (so-called amyloid enhancing factor) together with a single profound acute phase stimulus (subcutaneous injection of silver nitrate) [59]. All control animals developed appreciable splenic amyloidosis within 48 h. In contrast all mice in which circulating SAP had been completely removed by administration of adequate doses of sheep anti-mouse SAP antiserum failed to develop any detectable amyloid deposits. A further control group which received sheep antiserum to mouse C3, an unrelated serum protein not involved in amyloidosis, almost all developed amyloid.

The sheep antisera were raised by immunisation with the respective isolated pure mouse proteins [62,63]. The IgG fraction, separated by DEAE-Sephacel ion exchange chromatography, was used for injection into the mice.

These in vivo studies confirm that the mechanism of action of the anti-mouse SAP is indeed via SAP depletion, and show that SAP is required for amyloidogenesis. This may reflect the need for SAP to protect newly formed fibrils from proteolysis, as indicated by the work on protection of fibrils from proteolysis described above, or there may be a direct role for SAP in amyloid fibrillogenesis which has not previously been suspected. In any case the results again focus attention on inhibition of SAP binding to amyloid fibrils as a most attractive target for therapeutic attack in all forms of amyloidosis. A suitable inhibitory agent will act prophylactically to prevent development of the common age-associated diseases caused by amyloid deposition, especially AD and type II (maturity onset) diabetes mellitus.

Recently we reported the crystallisation of SAP in conditions that induce a reversible dissociation of the decamer into a pentameric form [15]. We now report the X-ray analysis of the crystals at 2 Å resolution, defining the complete three-dimensional structure of the pentamer. Intriguingly this human plasma protein has a tertiary fold which resembles that of the legume C-type lectins, concanavalin A and pea lectin. There are two calcium sites and these are shown to be involved in binding of carbohydrate and the synthetic ligand phosphoethanolamine. However, the calcium sites in SAP and the calcium and manganese sites of concanavalin A differ in their relationship to the common topology. The SAP pentamer shows nearly perfect five-fold symmetry and sequence comparisons suggest that very similar interactions are retained in CRP pentamers.

As indicated above, the present invention is based in part on the resolution of the complete three-dimensional structure of SAP, which is described in detail below. The knowledge of the structure of SAP, especially the key ligand binding sites, enables the design of therapeutic and diagnostic agents.

The present invention provides a method of designing molecules having a particular structural relationship to a protein molecule, especially to an active site or a binding site of the protein, the method utilising the three-dimensional structure of the protein, characterised in that the protein molecule is human SAP. The present invention also provides the use of the three-dimensional structural model of human SAP as the basis for molecular modelling of molecules having a particular structural relationship with human SAP.

The present invention also provides a method of producing a molecule having a structural relationship to a protein molecule, the method comprising (i) using the three-dimensional structure of the protein as the basis for the design of the molecule, and then (ii) synthesising the molecule thus-designed, characterised in that the protein is serum amyloid P component and the molecule produced binds to the amyloid fibril binding site on SAP or binds to amyloid fibrils.

The invention further provides a method for the production of a molecule that inhibits the binding of serum amyloid P component to amyloid fibrils, that is a binding site analogue or homologue or that is a high affinity substance, which comprises carrying out computer-aided molecular design using the three-dimensional structure of serum amyloid P component, synthesising the molecules thus designed and testing the molecules for the ability to inhibit binding of serum amyloid P component to amyloid fibrils and/or the ability to bind to amyloid fibrils.

In a method of the present invention candidate molecules are generally tested for their ability to inhibit binding of serum amyloid P component to amyloid fibrils in vitro or to bind to amyloid fibrils in vitro, for example, using an assay method as described in detail in Example 1 herein or a modification thereof if binding to amyloid fibrils is to be tested.

In a method of the invention, candidate molecules may be obtained by carrying out computer-aided molecular design using the three-dimensional structure of serum amyloid P component, in particular the three-dimensional structure at and/or around the various binding sites and other sites described in more detail below, and then synthesising the molecules so-designed. One or more of the following are preferably used in the design of a candidate molecule: the final refined electron density of serum amyloid P component described herein and illustrated in FIG. 1; the ribbon drawing described herein and illustrated in FIG. 2; hydrogen bonding diagrams set out in FIGS. 3A, 3B, 3C and 3D; and one or more of the calcium and ligand binding sites described herein and illustrated in FIG. 4.

A molecule according to the present invention having a particular structural relationship with human SAP may be an analogue of an SAP ligand, for example, a ligand analogue capable of interacting specifically and with high affinity to the ligand binding site of SAP and most especially with the amyloid binding site. Alternatively, the molecule may be an analogue or a homologue of an SAP binding site, most especially the amyloid binding site, or another molecule having high affinity for amyloid fibrils.

The design of molecules having a particular structural relationship to part of a protein molecule, so-called "molecular modelling" is well established, see for example [16–20]. Any such method may be used according to the present invention.

With increasing power and decreasing prices, computers powerful enough for molecular modelling are now readily available commercially, for example, Evans and Sutherland and Silicon Graphics machines. Likewise, software packagers are also available, for example, LEAPFROG (available from Tripos Associates, 16995 Hanley Road, Suite 303, St. Louis, Mo. 63144, USA), which suggests improvements to existing proposed molecules (OPTIMIZE), proposes new molecules expected to have good binding (DREAM) and supports interactive design (GUIDE). LEAPFROG is part of a larger software package involving protein modelling capabilities encoded in COMPOSER, which has been written by Professor Tom Blundell and colleagues at Birkbeck College, London, and is also available from Tripos Associates. COMPOSER is itself part of a comprehensive package known as SYBYL for computer modelling and design aimed at the pharmaceutical industry. Use of such software enables modelling of related proteins to assist the understanding of the specificity of the calcium mediated binding of pentraxins. Molecular modelling is becoming more and more widely used. The techniques generally used involve detailed investigations of the shape, charge distribution and the distribution of hydrophobic groups, ionic groups and hydrogen bonding at the site of interest. Automated systems available commercially greatly facilitate such investigations and assist in the design of molecules having particular desired characteristics. Alternatively, a ligand that is competitive with a natural ligand may be designed.

In the present case, the process of the structure-based design starts from the knowledge of the three-dimensional structures of SAP particularly when complexed to the ligands PE (phosphoethanolamine) and especially MOβDG (4,6-O-(1-carboxyethylidene)-β-D-galactopyranoside). The binding site of the ligand MOβDG is particularly important because our work has shown that binding of SAP to amyloid fibrils is inhibited by MOβDG, that is to say, MOβDG binds at or near the amyloid binding site of SAP.

The three-dimensional structure is illustrated in FIGS. 1 to 4 of the accompanying drawings and is described in detail below. The ligands MOβDG and PE bind via calcium atoms. Knowledge of the calcium binding site is therefore important, as is the topology of patches of basic residues adjacent to the calcium binding site, which patches may be also involved in binding larger molecules, for example, amyloid fibrils or DNA. Calcium (1) is co-ordinated to the side-chains of Asp58, Asn59, Glu136, Asp138 and the main chain carboxyl of Gln37, as shown in FIGS. 4a and 4b. The topology at and around the region of the calcium binding site is therefore particularly important in the design of therapeutic and diagnostic agents.

Structure-based design begins by delineating the surface of SAP that interacts with MOβDG (and PE) and which may be involved in the more extensive interactions with amyloid. The structure at that region is described in detail below. The shape, charge distribution and the distribution of hydrophobic groups and hydrogen bonding in that region are determined in detail. That information enables the design of ligands, in particular those that form hydrogen bonds to the hydroxyl groups of Tyr64 and Tyr75. Such design may be carried out using appropriate computer hardware and software, as described above, for example, using an Evans and Sutherland or Silicon Graphics machine and commercially available software packages, for example, COMPOSER. Use of appropriate software enables visualisation of the molecular interactions.

A second approach involves greater analysis of the surface binding characteristics of SAP. A range of automated methods are available for exploring binding sites for hydrophobic and ionic groups and to design molecules that will bind to binding sites and to active sites. An example of suitable software for this purpose is the LEAPFROG unit of COMPOSER, which suggests improvements to existing proposed molecules (OPTIMIZE), proposes new molecules expected to have good binding (DREAM) and supports interactive design (GUIDE). COMPOSER enables modelling of related proteins to assist the understanding of the specificity of the calcium-mediated binding of pentraxins.

As indicated above, molecular modelling may be used to design molecules that inhibit the binding of serum amyloid P component to amyloid fibrils. By investigating the binding sites, for example, the MOβDG (and PE) binding site, and the calcium binding site specific inhibitory ligands may be designed. The in vitro investigations described above show that MOβDG inhibits the binding of SAP to amyloid fibrils. The putative amyloid fibril binding site is therefore at or in the region of the MOβDG binding site. MOβDG binds via calcium atoms, so the calcium binding site, described in detail herein and illustrated in FIGS. 4a and 4b, is a particularly suitable site for molecular modelling. The regions of basic residues adjacent to the calcium binding site may be involved in the binding of molecules larger than MOβDG, for example, amyloid fibrils, so the region around the calcium site may also be used in molecular modelling.

A molecule of the present invention may therefore be a molecule which interacts with serum amyloid P component at and/or around the calcium binding site illustrated in FIGS. 4a and 4b. Such a molecule may, for example, interact with one or more of the residues Asp58, Asn59, Glu136, Asp138 and Gln37 of human serum amyloid P component or with the equivalent residues in serum amyloid P component of another species and/or with one or more basic residues in the region of those residues.

A molecule of the present invention is preferably bound with high affinity by SAP. For example, a molecule of the present invention may advantageously be based on the interactions of MOβDG with SAP but have more interactions with SAP (at or around the calcium binding site) than does MOβDG.

A molecule of the present invention may form hydrogen bonds to the hydroxyl groups of Tyr64 and Tyr75 of human serum amyloid P component or the equivalent residues in serum amyloid P component of another species.

A molecule of the present invention may be a physiologically tolerable structural analogue of a serum amyloid P component ligand, for example, of MOβDG or of phosphoethanolamine.

A further type of molecule of the present invention is one that causes inhibition of SAP binding to amyloid fibrils not by binding at the ligand binding site but by an allosteric reaction, which causes the binding site to be non-functional. The use of a binding inhibition assay, for example, as described in Example 1 below, reveals such molecules.

The use of a molecule of the present invention will result inter alia in removal or displacement of SAP from amyloid deposits and should then enable the body to mobililse and remove the amyloid fibrils, a process which has been shown to occur if new amyloid fibril synthesis is halted [21–25].

Knowledge of the ligand binding sites, especially as described above, enables analogues and homologues of those binding sites to be produced. The term "homologue of a binding site" is used herein to denote a peptide or polypeptide structure that is identical to a native SAP binding site or that differs from the native structure by conservative substitutions only (homology). Such a peptide or polypeptide may be synthetic or recombinant. A homologue of a ligand binding site will generally be a linear sequence that is identical or homologous to a native sequence and that folds into the correct conformation. However, a homologue of a ligand binding site may also be a topological homologue, that is to say, the amino acid sequence of the homologue comprises residues that form the three-dimensionsal structure of the binding site but that are not contiguous in the native linear sequence.

An analogue of a ligand binding site is a structure that is capable of binding the ligand even though it bears no likeness to the native binding site. An analogue may mimic the three-dimensional structure of the binding site or may bind the ligand in some other way. An analogue may comprise an amino acid sequence or may comprise other chemical entities, for example, nucleic acids, sugars or synthetic organic chemical molecules. Generally applicable methods for making analogues of structures are known, for example, as "combinatorial chemistry" see, for example [60].

The essential requirement of any analogue or homologue of the present invention is that it is capable of binding to amyloid fibrils. Examples of preferred binding sites for the production of analogues and homologues are the calcium binding site of serum amyloid P component illustrated in FIGS. 4a and 4b, and an analogue or homologue preferably includes structures around the calcium binding site, especially patches of basic residues.

The present invention also provides a low molecular weight polypeptide or any other molecule, for example, an oligonucleotide or oligosaccharide or small organic molecule that has high affinity for amyloid fibrils. Such polypeptides and other molecules may be designed on the basis of the three-dimensional structure of SAP or may be obtained by screening candidate molecules obtained either on the basis of a stereochemical relationship to SAP or by non-selective searching of libraries of synthetic, recombinant or naturally-occurring chemical compounds. Such libraries may be produced by combinatorial chemistry. Again, the efficacy of candidate molecules can be assessed using an inhibition assay, for example, as described in Example 1 below. It is necessary that any such polypeptide or other high affinity molecule to be used in vivo and also any binding site analogue or homologue to be used in vivo should not have the proteinase resistance and the protective capacity of SAP itself.

Antibodies that bind selectively to a ligand binding site of SAP and that inhibit SAP binding to amyloid are also part of the present invention. Such antibodies may be monoclonal antibodies or antibody fragments generated by chemical or recombinant techniques.

Any of the various embodiments of the present invention (a binding site inhibitor ligand, a binding site analogue or homologue, a low molecular weight polypeptide or other molecule having high affinity for amyloid fibrils or an antibody) that is physiologically tolerable and that inhibits binding of SAP to amyloid fibrils or that displaces SAP from amyloid fibrils may be used as a medicament according to the present invention. Such agents are useful for the treatment and/or prophylaxis of amyloidosis of any form, particularly common age-associated disease caused by amyloid deposition, for example, Alzheimer's disease and type II (maturity onset) diabetes mellitus.

Such agents may also be used as molecular delivery systems for the localization of other pharmaceutically active compounds at amyloid fibrils.

Administration of such an agent of the invention as a therapeutic agent or as a molecular delivery system may be enteral or parenteral. The oral route is generally preferred, provided the agent is not inactivated in the gastro-intestinal tract. (The oral route is generally unsuitable for the administration of proteins and polypeptides.) For diagnostic imaging such an agent, carrying an appropriate imaging label (see below), is generally administered intravenously or intrathecally.

For oral administration an agent of the present invention in admixture or conjunction with a pharmaceutically suitable carrier is preferably brought into unit dosage form, for example, as tablets, hard gelatin capsules or soft gelatine capsules. For parenteral administration, for example, by the intravenous or intrathecal route, an agent of the invention may be admixed with a suitable carrier, for example, a sterile isotonic solution or may be provided in lyophilised form. It may be necessary to take particular care with a diluent for use with a lyophilised imaging agent. Methods for preparing pharmaceutical preparations of all types, and suitable carriers and other ingredients for use in pharmaceutical preparations are well known and are described, for example, in Martindale's Extra Pharmacopoeia.

The present invention also includes a method of treatment and/or prophylaxis of amyloidosis, which comprises administering an effective amount of a physiologically tolerable binding site inhibitor ligand, a binding site analogue or homologue, a low molecular weight polypeptide or other molecule having high affinity for amyloid fibrils or an antibody of the present invention to a subject having or susceptible to amyloidosis.

A further aspect of the present invention is the in vivo diagnosis of amyloidosis. For this purpose a physiologically tolerable binding site inhibitor ligand, a binding site analogue or homologue, a low molecular weight polypeptide or other molecule having high affinity for amyloid fibrils or an antibody of the present invention is labelled with a tracer that is detectable in vivo. Such tracers are well known and include radioisotopes of iodine, indium and technetium, for example $^{123}$I, $^{131}$I, $^{124}$I, $^{111}$In and $^{99m}$Tc. Magnetic resonance tracers are also suitable. The labelled compound is administered to the patient, generally intravenously or intrathecally, and the patient is then subjected to the appropriate imaging process, and the labelling, if any, of amyloid deposits is noted for use in diagnosis.

Particularly useful for diagnostic purposes are molecules according to the present invention that are capable of crossing the blood-brain barrier and hence of labelling amyloid deposits in the brain, thus enabling diagnosis of Alzheimer's disease. At present there is no diagnostic test for this, the fourth most common cause of death in the Western world. Low molecular weight polypeptides or other high affinity low molecular weight molecules may be designed specifically to cross the blood-brain barrier. (Low molecular weight polypeptides may comprise, for example, 3 to 50 amino acid residues. Other high affinity low molecular weight molecules may have a mass of, for example, up to 5000 to 6000 Daltons.) Such peptides and other molecules are much cheaper than natural SAP and obviate all the problems associated with isolation, safety and availability of the human blood protein. Those problems have hitherto prevented SAP being taken up as a commercial product in spite of its undeniable clinical value, and the use of SAP in diagnosis is currently confined to research centres.

A further use for analogues and homologues of SAP binding sites is for the screening of potential therapeutic agents, for example, using a test for inhibition of binding to amyloid fibrils.

As indicated above, by investigating the binding sites, for example, the MOβDG and PE binding site, ligands may be designed that, for example, have more interactions with SAP than do MOβDG or PE. Such ligands will bind to SAP with higher affinity and so function as competitive ligands with regard to amyloid and thereby remove SAP from amyloid. Removal of SAP from the deposits may then enable the body to mobilise and remove the amyloid fibrils, a process which has been shown to occur if new amyloid fibril synthesis is halted [21–25].

Synthetic or recombinant proteins homologous or analogous to the ligand binding site of native SAP may be designed as may other molecules having high affinity for amyloid fibrils. Such molecules should also be capable of displacing SAP from amyloid and provide a protective effect.

As indicated above, the knowledge of the SAP binding site enables synthetic binding site homologues and analogues to be designed. Such molecules will facilitate greatly the use of the unique amyloid binding properties to target potential therapeutic agents into amyloid deposits. They may also be used to screen potential therapeutic agents. Furthermore, they may be used as immunogens in the production of monoclonal antibodies according to the method of Köhler & Milstein [61] and subsequent modifications, which antibodies may themselves be used in diagnosis and/or therapy.

BRIEF DESCRIPTION OF THE DRAWINGS

FIG. 1: Final refined electron density map of SAP.

FIG. 2: Ribbon drawings generated with Setor [26].

FIG. 4: The clacium and ligand binding sites in SAP:

DETAILED DESCRIPTION OF THE DRAWINGS
(FIGS. 1 to 4)

Note: FIGS. 5 to 8 are described in detail in Example 2 below.

Figure 1A:
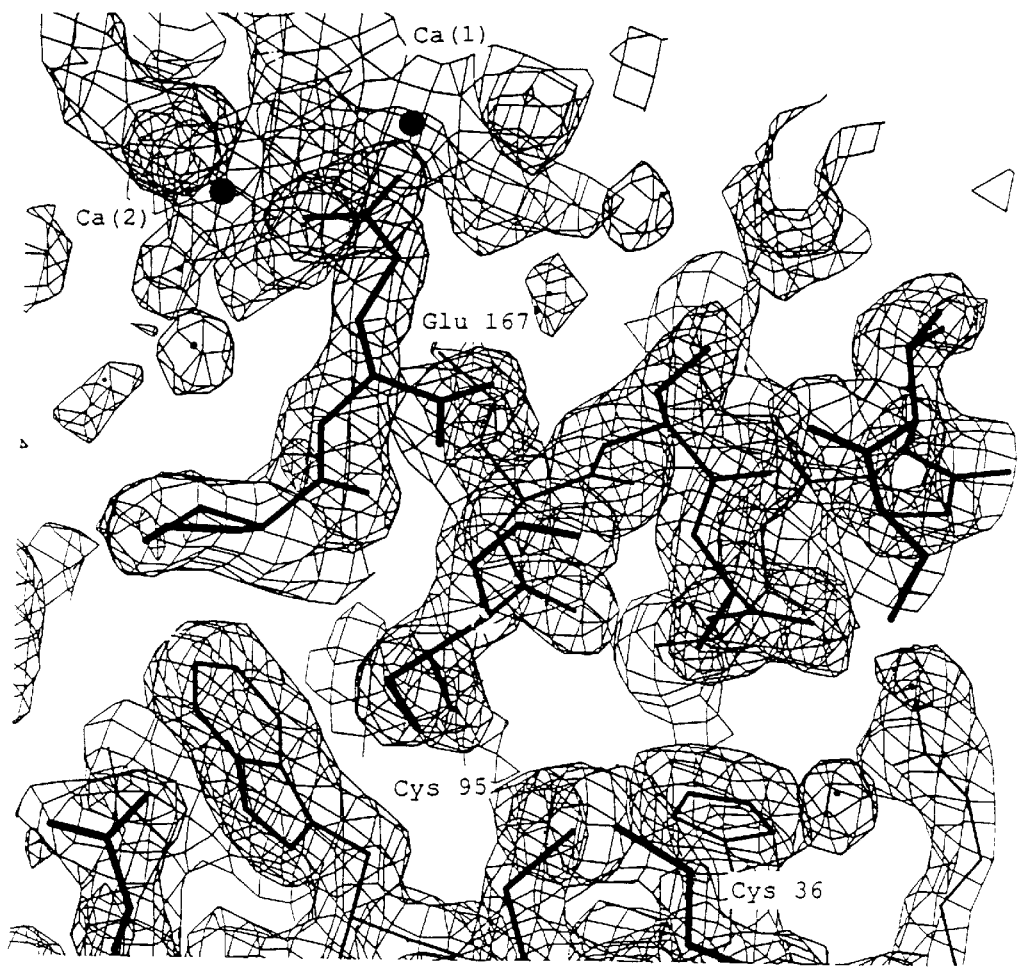
FIG. 1a: Refined electron density map (2Fo-Fc) calculated at 2 Å resolution and contoured at 1 r.m.s.
Figure 1B:
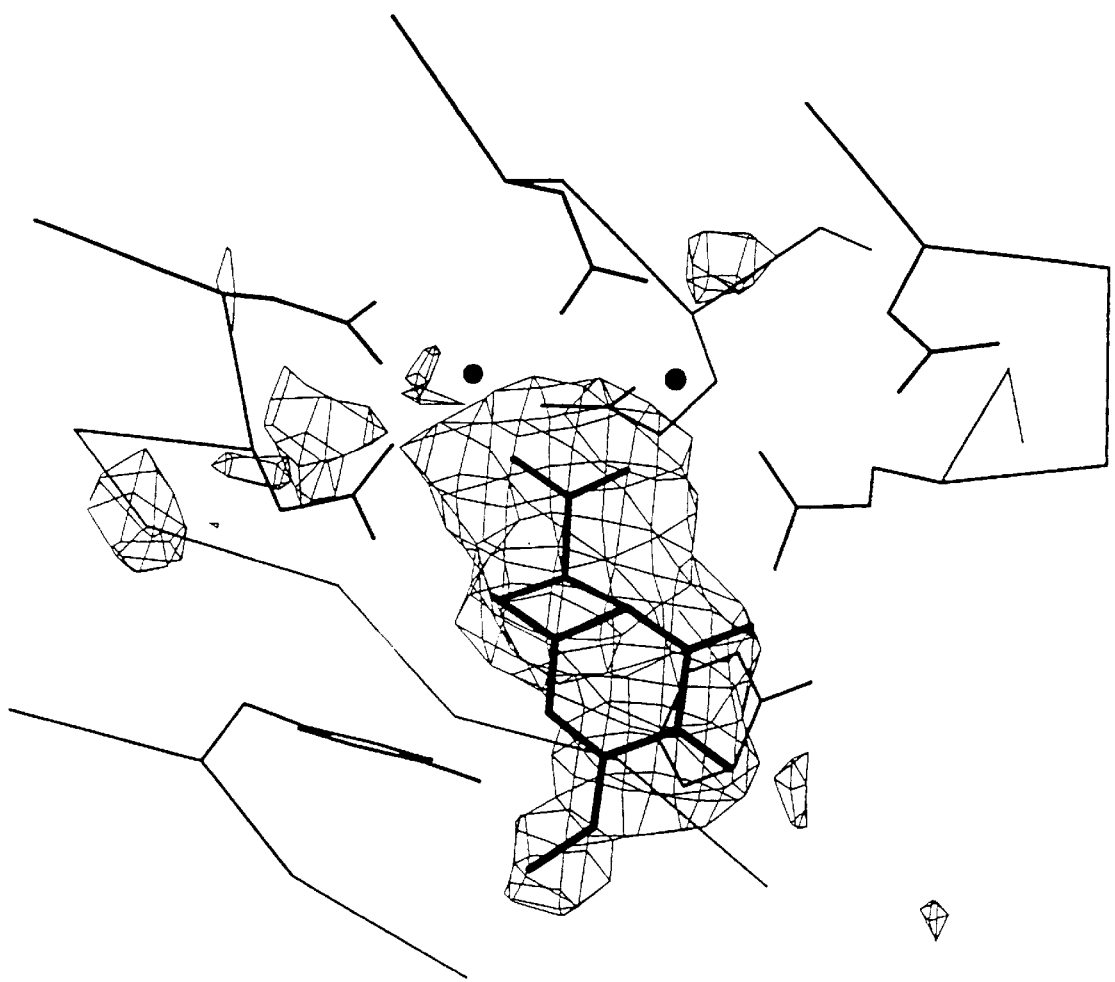
FIG. 1b: MOβDG complexed with SAP contoured at 1 r.m.s. electron density level at 2.9 Å resolution.
Figure 1C:
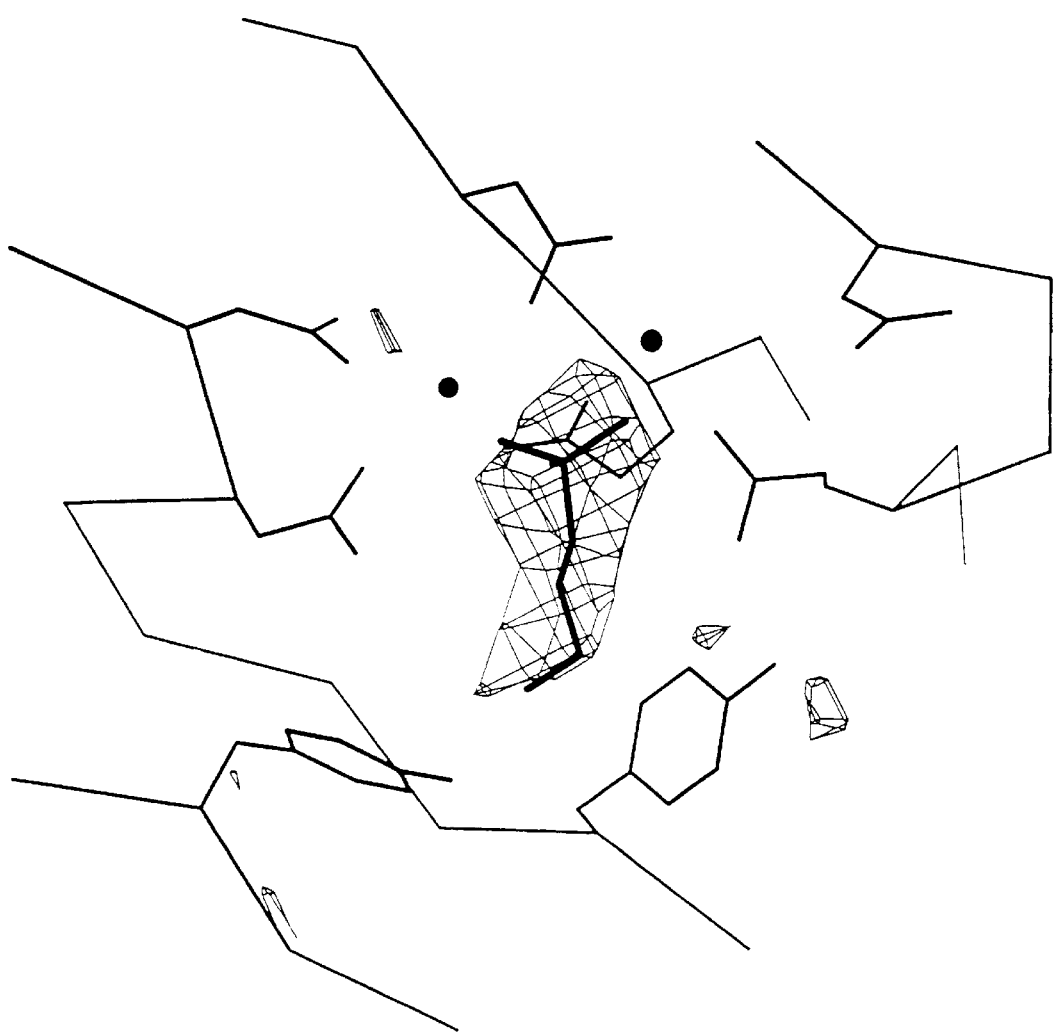
FIG. 1c, Phosphoethanolamine (PE) complexed with SAP contoured at 1 r.m.s. electron density level at 2.9 Å resolution.

FIGS. 1a, 1b, and 1c

Final refined electron density of SAP. a, Refined electron density map (2Fo-Fc) calculated at 2 Å resolution and contoured at 1 r.m.s. This illustrates the SAP helix packing against the β-pleated sheets in the region of the disulphide bridge Cys36-Cys95. The top left hand of the diagram illustrates a region where the side chain Glu167 contacts the calcium binding site of a symmetry-related molecule. The region of the calcium ions is contoured at 5 r.m.s. showing that the glutamate bridges the two ions in a manner similar to the acetate ion. b, MOβDG complexed with SAP contoured at 1 r.m.s. electron density level at 2.9 Å resolution. Crystals of SAP prepared by the batch method [15] in the presence of MOβDG were isomorphous with crystals of native SAP and had cell dimensions a=69.06 Å, b=99.3 Å, c=96.75 Å and β=95.84°. Data were collected on a MAR imaging plate system mounted on a Siemens XP-18 rotating anode and a final $R_{Merge}$ of 5.3% was obtained. Data were 95.8% complete to 2.9 Å resolution. A final crystallographic R factor of 0.197 for all reflections in the range 10–2.9 Å was obtained after refinement in XPLOR without non-crystallographic restraints. The success of this experiment depended on soaking in an excess of the sugar in order displace the acetate ion which otherwise occupies the same position at the calcium-binding site. The MOβDG is well defined only in protomer 3, shown here, where it is involved in a crystal contact. c, Phosphoethanolamine (PE) complexed with SAP contoured at 1 r.m.s. electron density level at 2.9 Å resolution. Crystals of SAP prepared by the batch method [15] in the presence of 9 mM PE were not isomorphous with crystals of native SAP and had cell dimensions a=67.05 Å, b=103.43 Å, c=102.43 Å and β=95.73°, in space group P2$_1$. Data were collected on a MAR imaging plate system mounted on a Siemens XP-18 rotating anode and a final $R_{Merge}$ of 6.4% was obtained. Data were 95.5% complete to 2.9 Å resolution. In the initial refinement the SAP pentamer was treated as single rigid body and R factor of 0.332 was obtained for the 3513 reflections between 30–6 Å. The five subunits were then treated as individual rigid bodies and refinement produced an R factor of 0.264 for the 11628 reflections between 18–4 Å. The final crystallographic R factor of 0.199 for all reflections in the range 10–2.9 Å was obtained after refinement in XPLOR; non-crystallographic symmetry restraints were not applied.

Figure 2A:
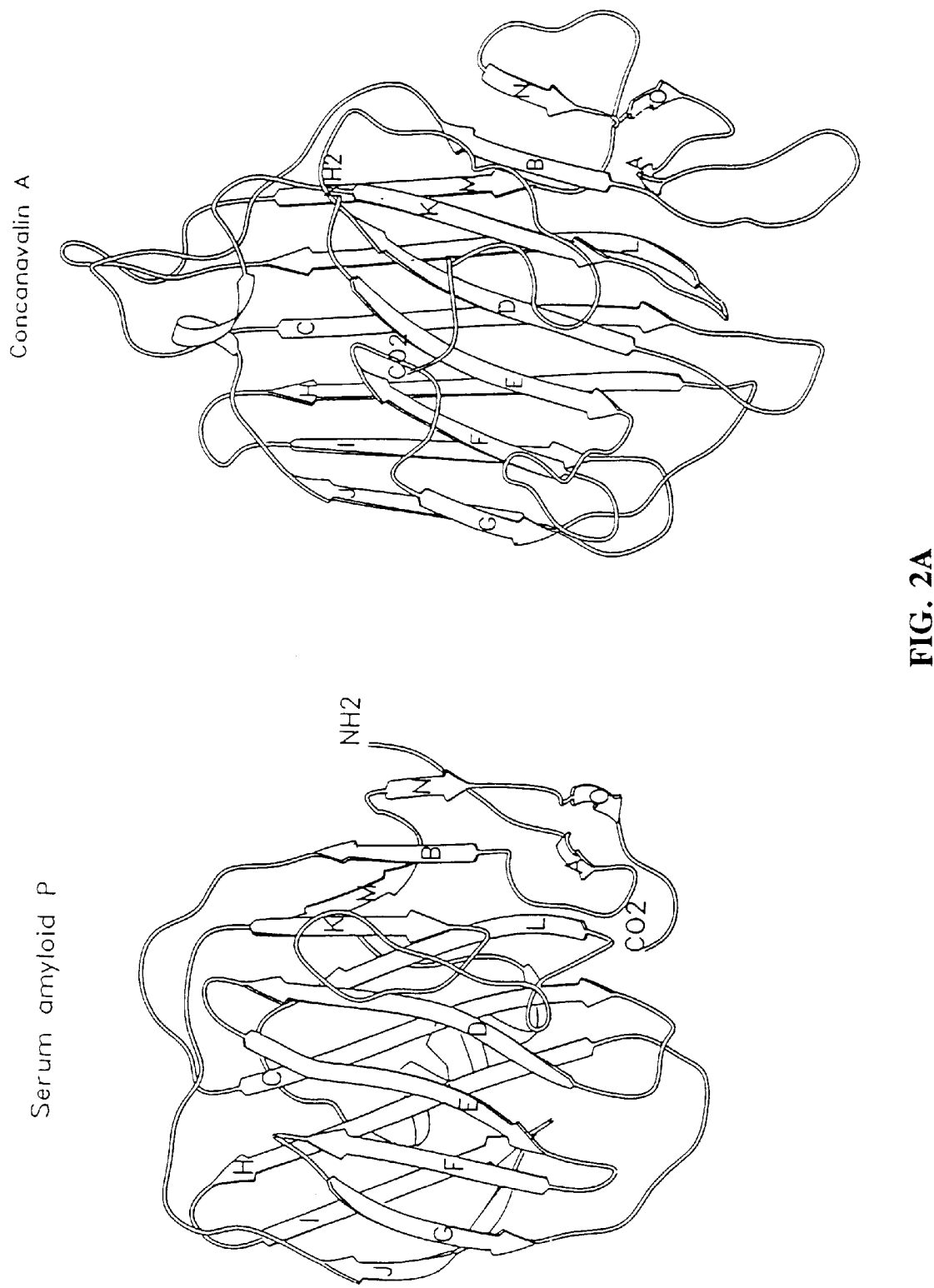
FIG. 2a, The topology of SAP compared with the legume C-type lectin concanavalin A (conA).
Figure 2B:
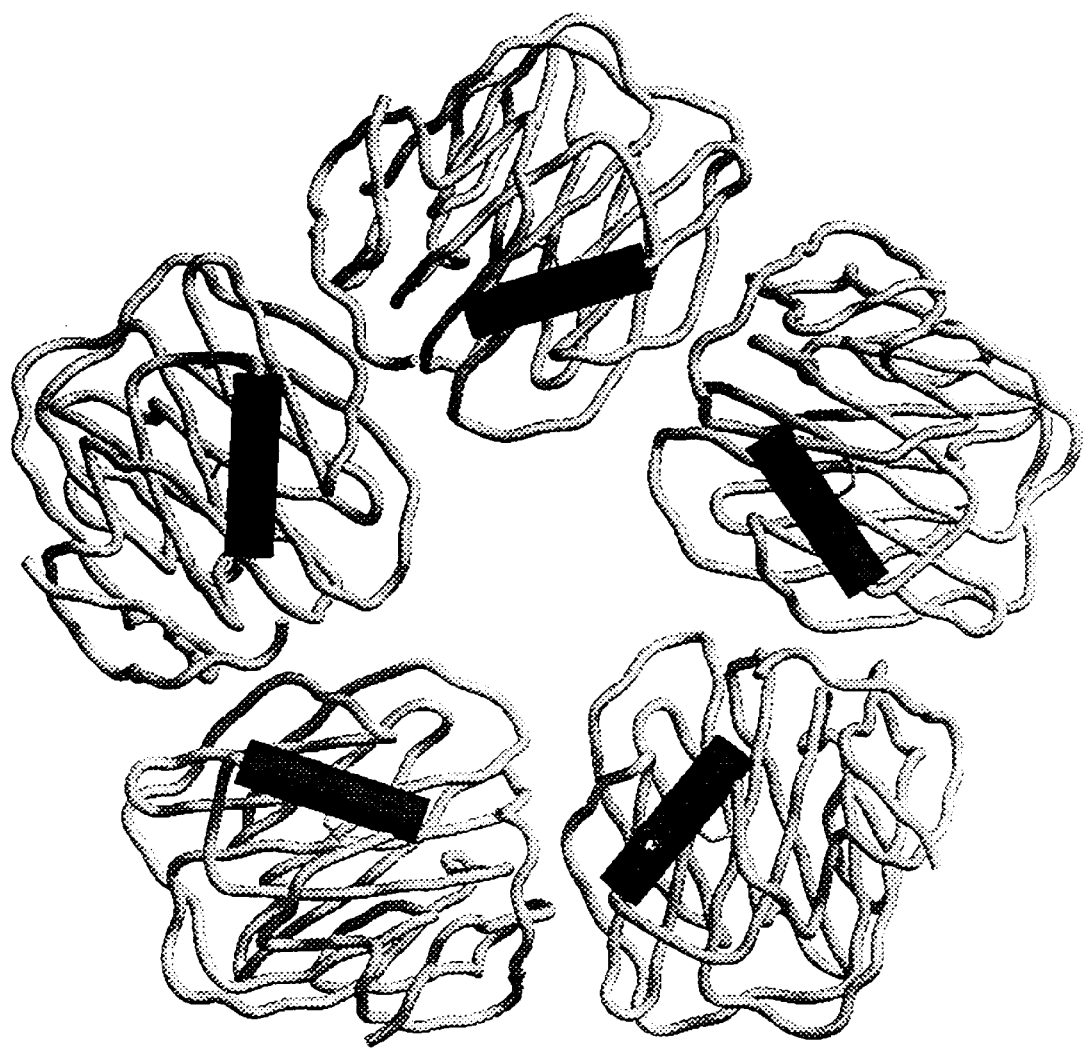
FIG. 2b, Structure of the pentamer of SAP viewed along the non-crystallographic five-fold axis of symmetry.
Figure 3A:
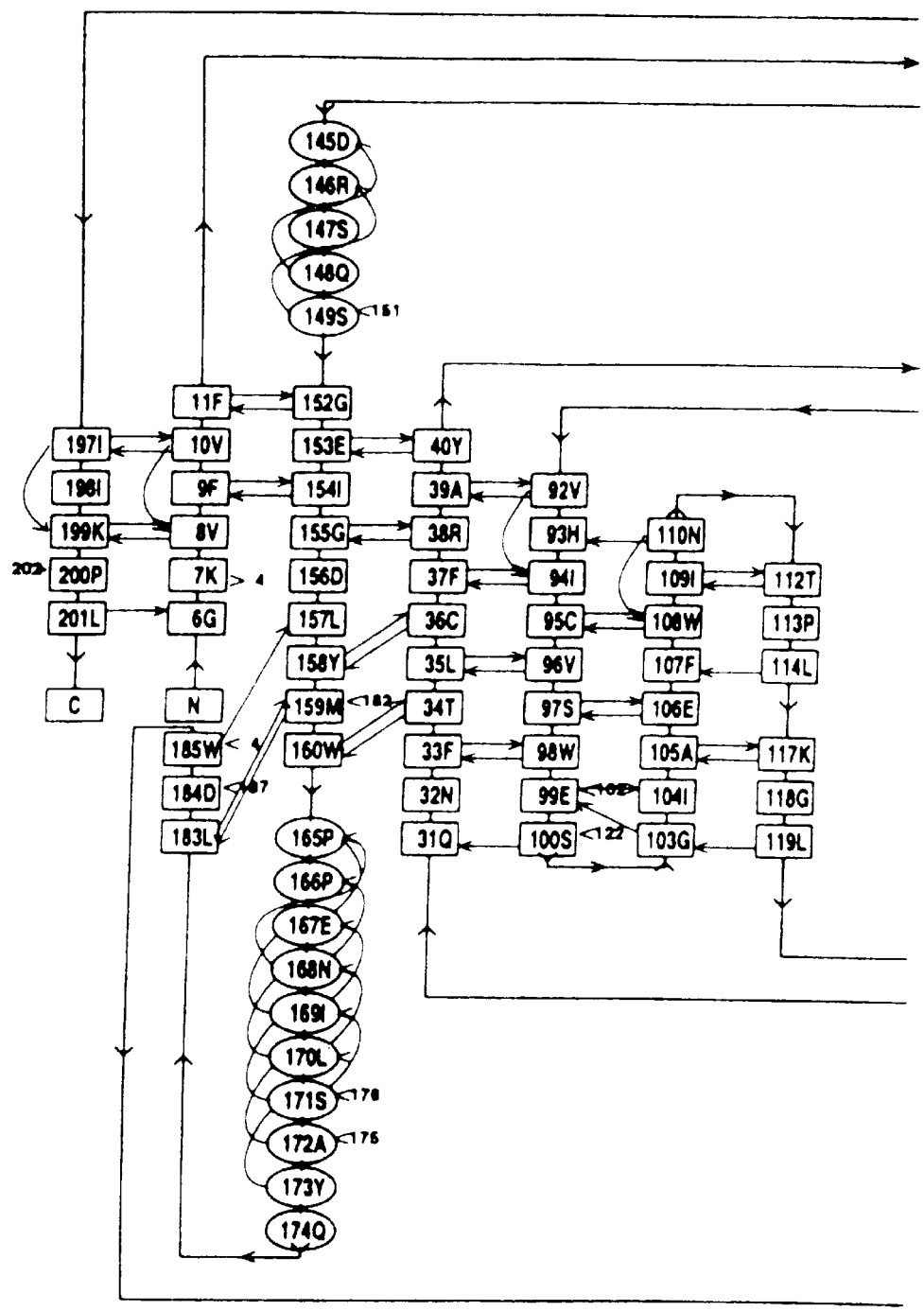
FIGS. 3A, 3B, 3C and 3D: Hydrogen bonding diagrams generated by HERA [27] for SAP (above) and pea lectin (Brookhaven code 2LTN) (below).
Figure 3B:
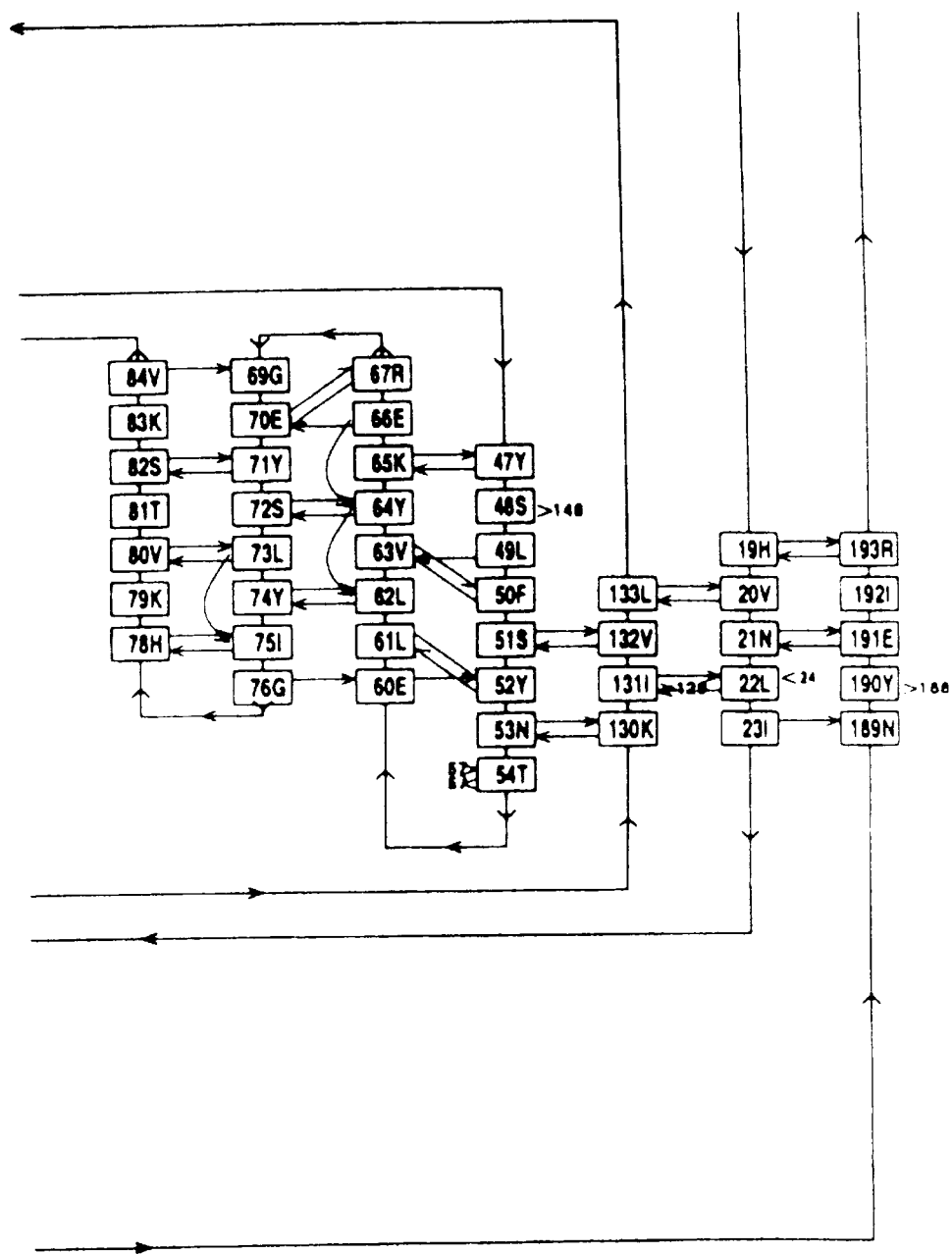
Figure 3C:
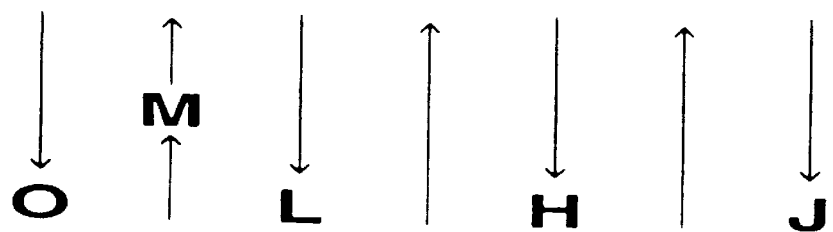
Figure 3C:
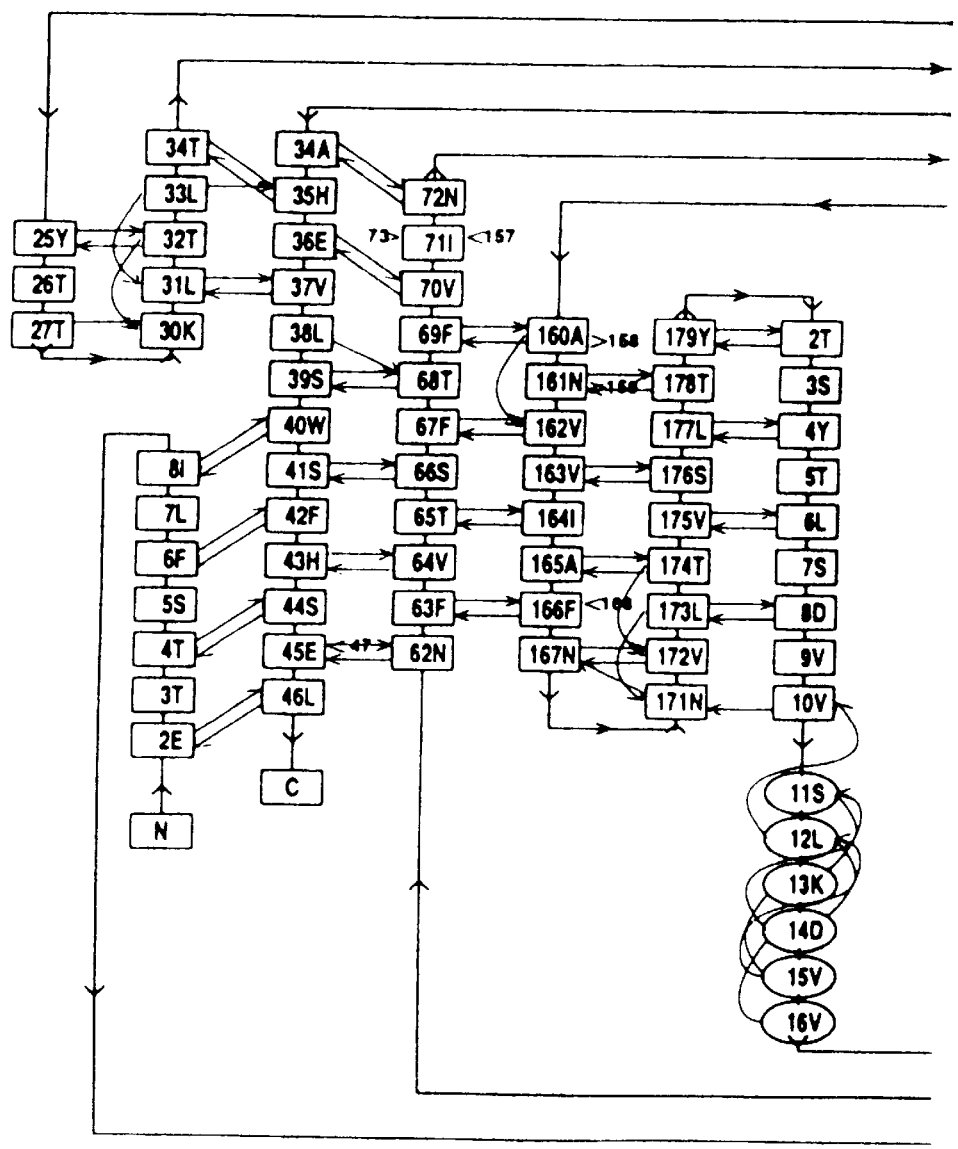
Figure 3D:
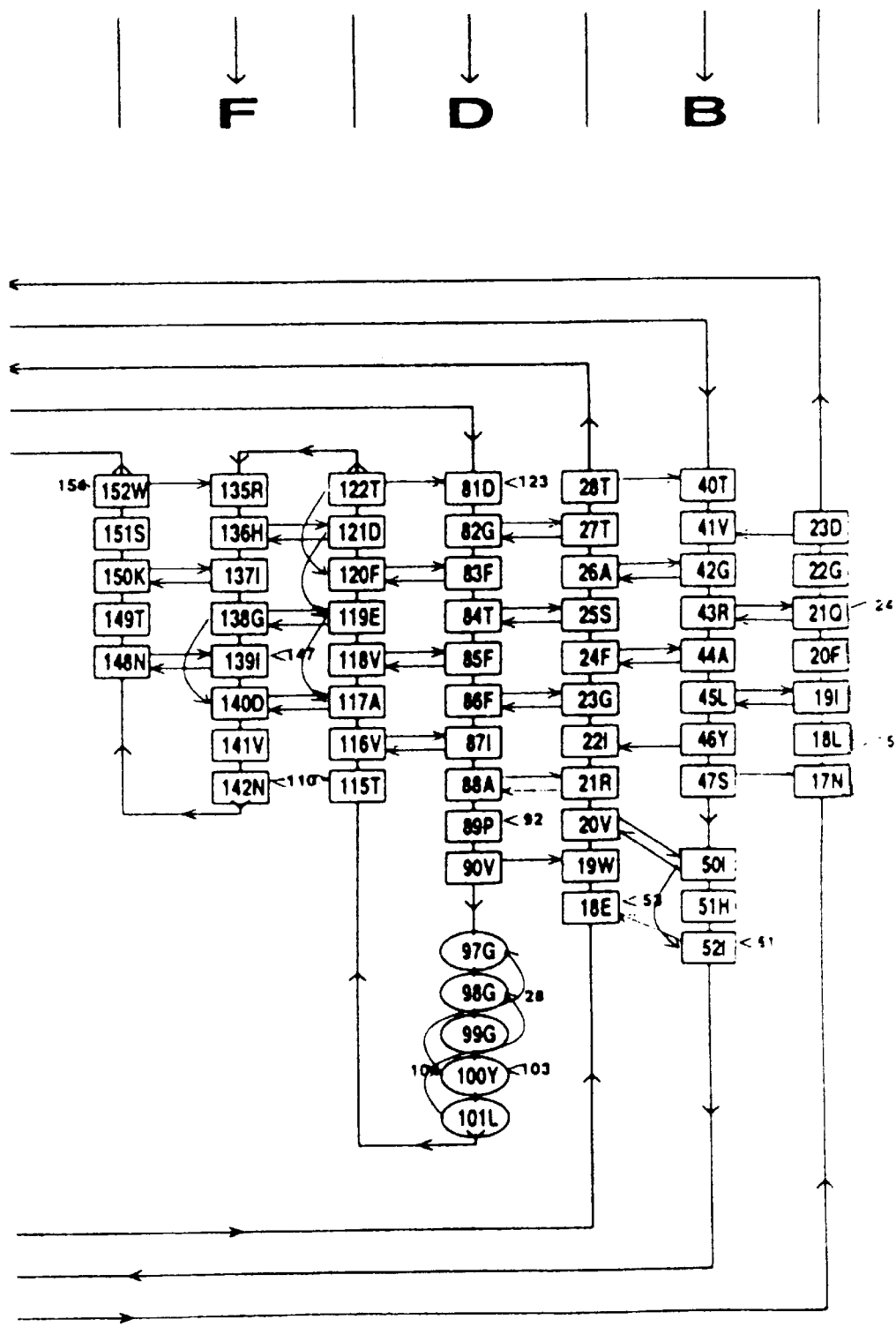

FIGS. 2a and 2b

Ribbon drawings generated with Setor [26]. a, The topology of SAP compared with the legume C-type lectin concanavalin A (conA). The strands are labelled from the N-terminus of SAP, ABCDEFGHIJKLMNO, with structurally equivalent strands in conA labelled similarly. The positions of the N- and C- termini in conA are altered with respect to the nascent protein by ligation of the original N- and C- termini and proteolytic cleavage between strands D and E. The two structures can be superimposed by a least squares fit using the Cα positions of the two sets of anti-parallel sheets to produce an r.m.s. deviation of 2.4 Å. This is due to a greater angle between these sheets in SAP than conA. b, Structure of the pentamer of SAP viewed along the non-crystallographic five-fold axis of symmetry. The pairwise r.m.s. deviations for all main chain atoms range from 0.19 Å between protomers 1 and 5 to 0.24 Å between protomers 3 and 4.

FIGS. 3A, 3B, 3C and 3D

Hydrogen bonding diagrams generated by HERA [27] for SAP (above) and pea lectin Brookhaven code 2LTN) (below). The secondary structural elements were assigned according to the criteria defined by Kabsch and Sander [29].

Figure 4A:
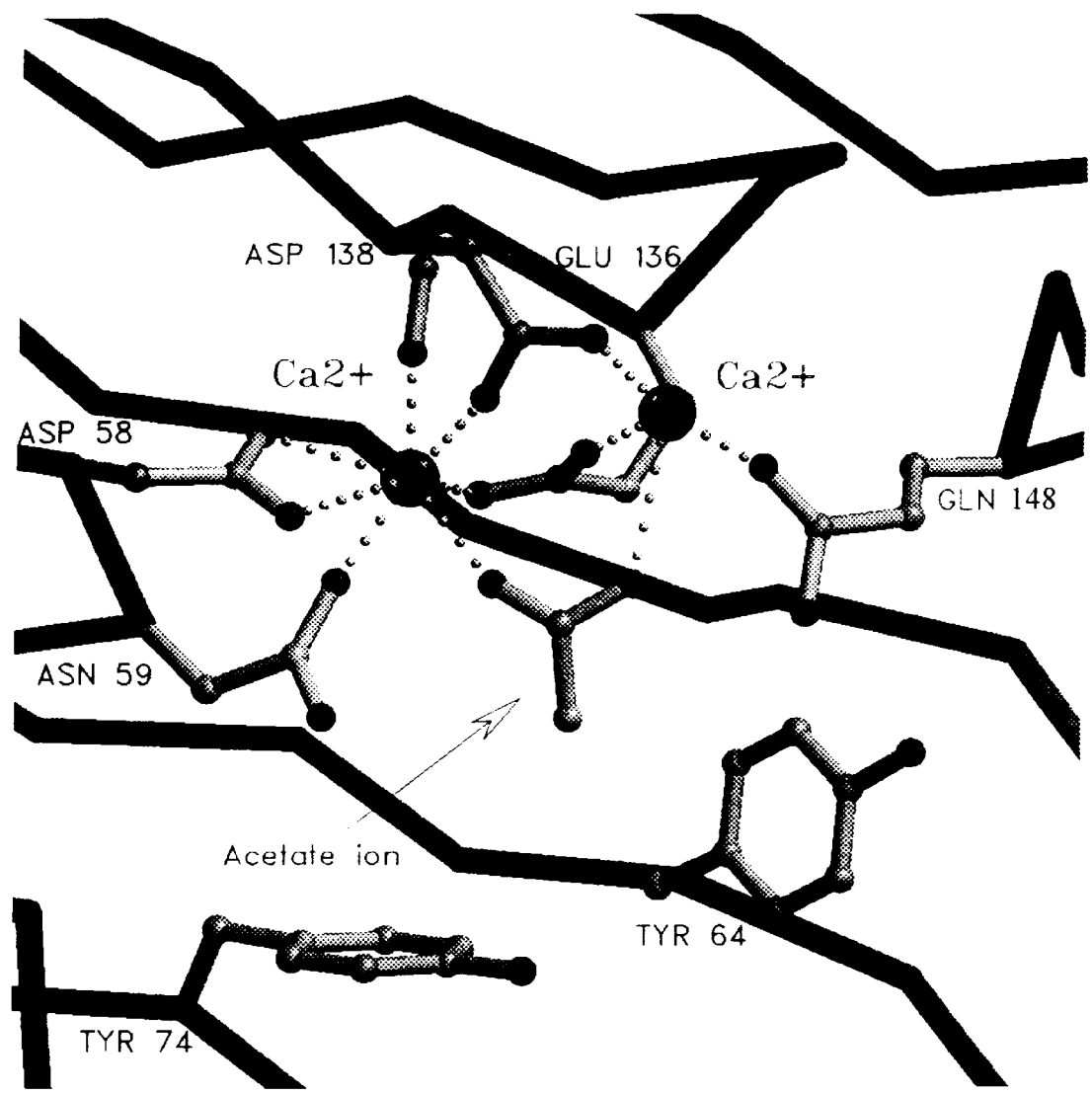
FIG. 4a, Topology around the calcium binding site showing the residues involved in calcium coordination and those in the hydrophobic pocket.
Figure 4B:
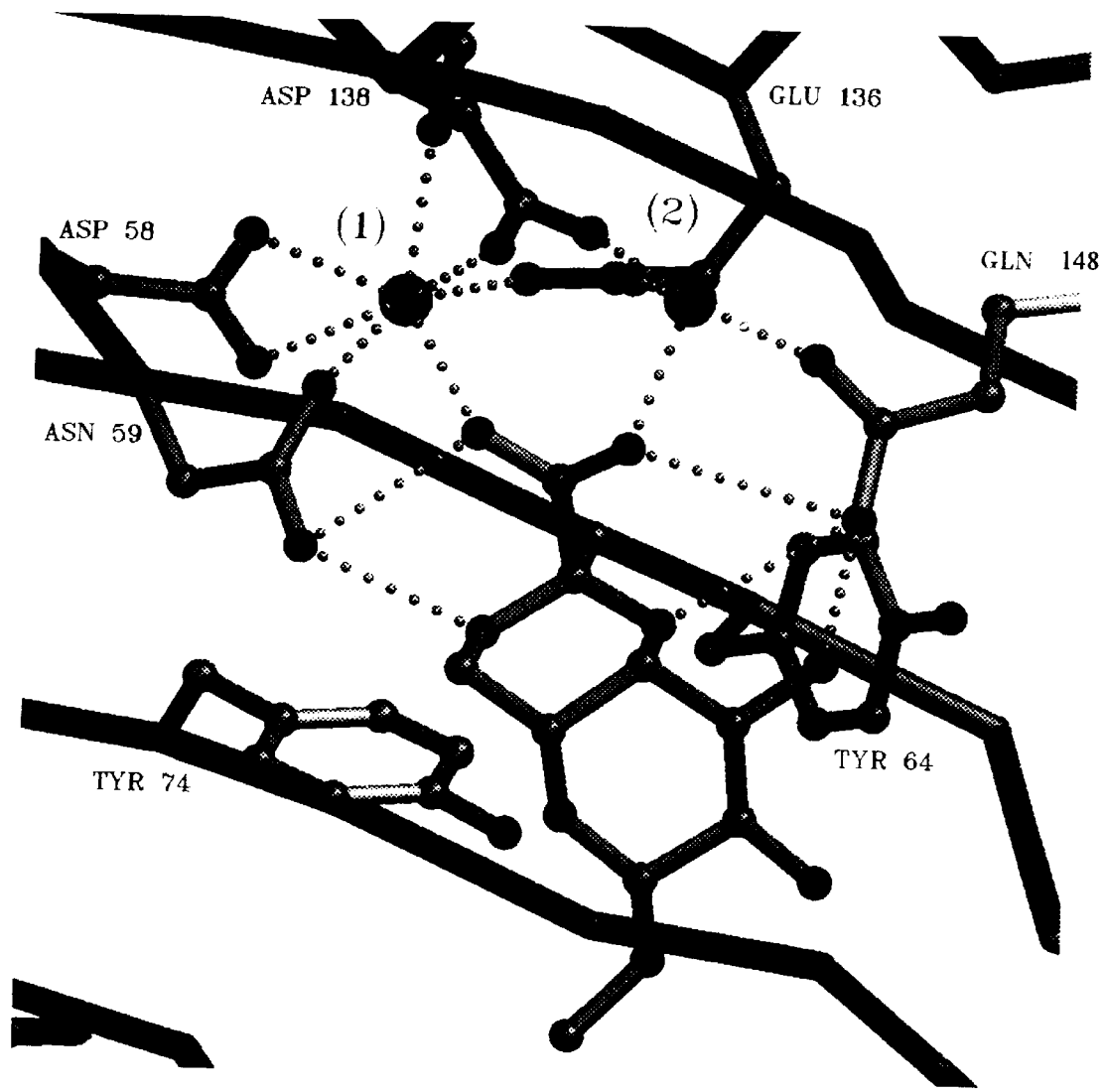
FIG. 4b, MOβDG binding site.

FIGS. 4a and 4b

The calcium and ligand binding sites in SAP. Diagrams generated using Setor [26] Important interactions between calcium ions, ligands and the protein are shown by dotted lines. a, Topology around the calcium binding site showing the residues involved in calcium coordination and those in the hydrophobic pocket, (Leu62, Tyr64, Tyr74) and the cleavage site (Phe144, Asp145) in SAP. Calcium (1) has heptagonal coordination, whilst Calcium (2) has hexagonal coordination. b, MOβDG binding site. The main interaction involves coordination between the calcium ions and the carboxylate of the carboxyethylidene ring. The amide nitrogens of Asn59 and Gln148 form hydrogen bonds to the 4,6 oxygens of the carboxyethylidene ring. The only interaction between the protein and the galactopyranoside ring is a hydrogen bond between the 3 oxygen and the amide nitrogen of Gln148.

DETAILED DESCRIPTION

Three-dimensional Structure

Serum amyloid P component was isolated at greater than 99% purity from pooled human ascites and pleural effusion fluids [31]. The crystals obtained at pH 5.5 in a medium containing calcium and acetate ions as described earlier [15] were of space group $P2_1$, and cell dimensions a=68.9 Å, b=99.3 Å, c=96.7 Å and β=95.9°. The initial model of pentameric SAP was based on X-ray analysis at 2.8 Å resolution using the multiple isomorphous replacement (MIR) technique followed by solvent flattening [32] and five-fold molecular averaging [33]. The refinement statistics are shown in Table 1, the legend of which gives further details of the X-ray analysis. The final model was refined at 2.0 Å resolution to an agreement (R) value of 0.18 to give a clear electron density for all residues of the five subunits (see FIG. 1a).

The SAP pentamer consists of five subunits of 204 amino acid residues, each with a closely similar three-dimensional structure constructed from anti-parallel β-strands (A-O) arranged in two sheets as shown in FIG. 2a. The tertiary fold can be envisaged as a jollyroll of strands ABCDKLNO, elaborated by the addition of three further anti-parallel strands (EFG and HIJ) forming a β-meander at the same end of each of the sheets to give the topology: +11−9+7−1−1−1−3+1+1+5−9−1+12−13. In this arrangement strands A and M are both hydrogen bonded to strand L as shown in FIGS. 3A, 3B, 3C and 3D. The disulphide between Cys36 and Cys95 links the two adjacent strands (L and C) of one β-sheet. A long α-helix between strands L and M is folded on top of this β-sheet. There is also an N-linked oligosaccharide at Asn32 on this sheet; only one saccharide residue is visible in the electron density.

The hydrophobic core between the two sheets is comprised mainly of tryptophans, tyrosines, phenylalanines and leucines. The core is closed off by two β-arches between the two sheets; strands joining B to C and J to K are hydrogen bonded and anti-parallel, an arrangement characteristic of proteins derived from a jellyroll motif. One end of the core, formed by 11 residues at the N-terminus and those in the N and O strands at the C- terminus (FIGS. 2, 3), has hydrophobic residues accessible to solvent. The other end of the core is involved in interactions with a neighbouring protomer (see below) and so is inaccessible to solvent.

Tertiary Fold Comparisons

The similarities of the amino acid sequences of SAP, human and Limulus CRP and female hamster protein suggest that they may have similar three-dimensional structures. Comparative modelling [34] shows that these pentraxins can have equivalent anti-parallel structures with insertions and deletions in the loops between the β-strands and α-helices (Srinivasan, N., White, H. E. & Blundell, T. L. unpublished results). It was found that most solvent-inaccessible aromatic side-chains are conserved to give compact hydrophobic cores in all members of the family.

The jellyroll topology of the pentraxins is reminiscent of that of the picornavirus coat proteins, which also have pentameric structures. However, pentraxins resemble most closely legume lectins such as concanavalin A [35] and pea lectin [36] (FIG. 2a). In each case the arrangement of strands is identical but the N- and C- termini are in different positions (FIGS. 3A, 3B, 3C and 3D). In pea lectin the N-terminus is at strand M and the C-terminus at strand L (labelling of the topologically equivalent strands follows those in SAP as shown in FIG. 3). The strands A and M are both hydrogen-bonded to strand L in a similar manner to those in SAP. In the three-dimensional structure of concanavalin A the N-terminus is at strand E and the C-terminus at the end of strand D due to a post-translational cleavage which follows ligation of the true termini between strands L and M [37]. Pea lectin is additionally cleaved at the loop connecting strands I and J.

Alignment of sequences on the basis of topologically equivalent features of the three-dimensional structures [29] shows that helices occupy different positions in the pentraxins and legume lectins and that the amino acid sequences of the two families have identities of only ~11%. The two main helices in SAP occur before and after strand L, whereas the helices in the legume lectins occur at the C-terminus of strand J. There is a long insertion between the end of the helix after strand D and the beginning of strand E in the lectins relative to the pentraxins. Strands G, H and L, together with the type IV β-hairpin between H and I, are identical in both SAP and pea lectin. The so-called pentraxin octapeptide signature sequence, H X C X S/T W X S (SEQ ID NO:1), is in this region, but this is not conserved in the legume lectins.

Structure of the Pentamer and Decamer

The structure of the pentamer is shown in FIG. 2b. The five subunits are arranged in a ring with a hole that is 20 Å in diameter and 35 Å deep at the centre. The two layers of β-strands in each subunit are in planes normal to the five-fold axis. Strands G, I, J of one protomer interact with strand N and loops between strands A and B, C and D, G and H, K and L of an adjacent protomer (FIG. 2b). When SAP is overlaid on the pea lectin, strand J does not give as good a fit as other strands. In SAP this strand has moved to provide inter-protomer contacts, with all residues between Pro113 and Leu119 being involved. The subunit interactions consist of hydrogen bonds between main chain peptide groups, three salt bridges and some hydrophobic contacts, in contrast to other pentameric systems where there are often inter-subunit β-sheets. The surface area of the protomer that is buried on formation of the pentamer is 410.5 Å$^2$, comprising 15.4% of the total surface of the protomer. The residues involved in these extensive interactions and which account for the considerable stability of the SAP pentamer have been determined.

In contrast the SAP decamer is readily dissociated by reducing the pH to 5.5. The simplest explanation for this is that the decamer is stabilised by ionic interactions involving carboxylate and/or imidazole groups. Electron microscopy has clearly shown that the SAP pentamers are packed face-to-face [38] and it seems probable that the faces in contact are those carrying the α-helix since we show (see below) that the calcium-dependent ligand-binding sites are on the other face and such binding is exhibited by the decamer. Furthermore adjacent sites are accessible to chymotryptic cleavage in the decamer in the absence of calcium ions. It is not clear which groups are involved in the decamer stabilisation although Glu167, positioned on the helix, is a likely candidate. A compact decamer can be modelled if the pentamer five-fold axes are in line but the subunits are out of step, allowing the helices from one layer to pack between those of the opposite layer. Structure analysis of a crystal form produced at neutral pH with ten protomers in the asymmetric unit is in progress.

The models of CRP and female hamster protein demonstrate that the pentamers can have very similar inter-subunit interactions. CRP of the invertebrate *Limulus polyphemus* is hexameric [39] and we have also been able to construct this arrangement of protomers by operating with a six-fold axis placed slightly further from the subunit than the five-fold axis of SAP.

Calcium Binding Site

In serum amyloid P component we have identified two large spheres of density which are too heavy to be oxygen atoms and are in positions that imply the presence of calcium ions, between 4.0 Å, and 4.3 Å apart in the five subunits and bridged by a common side-chains. Calcium (1) is coordinated to the side chains of Asp58, Asn59, Glu136, Asp138 and the main-chain carbonyl of Gln137 (FIG. 4a). Unlike many calcium-binding sites in proteins, such as parvalbumin, the coordinating residues come from different parts of the sequence. This is achieved by a distortion at the start of strand E carrying residues Asp58 and Asn59 and the region containing Glu136 and Asp138 looping over towards calcium (1) (FIG. 4a). The calcium ligation is likely to be an important local structural determinant. The seventh coordination site is occupied by a ligand that has the appearance of an acetate ion from the crystallisation buffer in protomers 1, 2, 4 and 5, but in protomer 3 this position is filled by the side-chain of Glu167 of an adjacent molecule in the crystal lattice. Glu136, Asp138 and the acetate/lattice contact form a bridge to a second, more loosely bound calcium ion (2). The coordination of calcium (2) is completed by Gln148 and two water molecules. In a cross-phase difference Fourier of cerium sulphate soaked crystals, we find that calcium (2) is displaced by a cerium ion. Calcium (2) is also removed when the crystals are soaked in calcium free buffers. These observations are consistent with the more solvent accessible position and fewer protein ligands of calcium (2).

Residues which provide ligands to the calcium ions are conserved in all SAPs but although Asp58 is found in hamster SAP, human CRP and Limulus CRP it varies in other CRPs. Nevertheless, the general organisation of the site is probably retained.

However, the disposition of these groups on surface loops where sequence differences accumulate could explain the considerable change in calcium affinity between CRP and SAP. Furthermore, in CRP there is evidence that both calciums bind with the same affinity at neutral pH [40] whereas in SAP our results show that site calcium (2) has fewer protein ligands and can be preferentially unloaded. The tighter calcium binding and equivalence of the sites in CRP could also be due to the substitution of Asp145 in SAP by glutamate in CRP. The longer side-chain in CRP would permit a full complement of protein ligands to calcium site (2).

The existence of two metal ions bridged by protein ligands is reminiscent of concanavalin A. However, although the metal binding sites in the legume lectins are on the same face of the protein, they are at a different position between strands E and F compared to D and E on SAP. There are no ligands of the two calciums that are topologically equivalent to those for the calcium and the manganese of the lectins. Thus, although there is evidence for divergent evolution of the protein folds of the plant lectins and the pentraxins, this is not supported by a conservation of similar metal binding sites.

Ligand Binding

SAP binds to methyl 4,6-O-(1-carboxyethylidene)-β-D-galactopyranoside (MOβDG) which is not recognised by CRP. FIG. 1b shows the electron density for MOβDG complexed with SAP. The sugar derivative binds directly through the acidic group to the two calcium ions in a similar way to the acetate which it replaces. The other interactions include two hydrogen bonds formed between the 4,6 oxygen atoms of the ring and the amide nitrogen atoms of Gln148 and Asn59 respectively, each of which bind to the calcium ions through their amide oxygens (FIG. 4b). Thus the role of calcium is not to bind the galactopyranoside ring directly but rather to mediate its binding by orienting side-chain amides in a way that resembles saccharide binding in lectins. There is only one hydrogen bond to the galactopyranoside ring (FIG. 4b). Thus it is the methyl 4,6-O-(1-carboxyethylidene) ring that forms the main interactions with the protein, explaining why neither the non-cyclic acetal of MOβDG nor the simple monosaccharides bind [3,10,26]. The R-isomer bridge methyl group points into a hydrophobic pocket formed by Leu62, Tyr64 and Tyr74. The differences in the hydrophobic pocket and the ligand distribution at the calciums in CRP may explain the poor binding to MOβDG. It is probable that this site is involved in binding to amyloid fibrils.

The highest affinity interaction of human CRP is its calcium-dependent binding to phosphocholine (PC). Studies carried out on human CRP [41,42] have implicated amino acid residues 50–60 in the ability to bind PC while more recent mutagenesis experiments [43] have identified Lys55 and Arg56 as key residues. The native SAP structure shows that Asp58 and Asn59 from this loop are involved in coordinating one of the two calcium ions. Human SAP, in contrast, does not bind to PC although in common with CRP it does bind to phosphoethanolamine (PE). The electron density maps for SAP co-crystallised with PE (FIG. 1c) show a major site in all subunits, which coincides with that which binds acetate ions and MOβDG and indicates a direct interaction between the phosphate group and both calcium ions. In contrast to MOβDG this interaction with PE displaces Glu167 from its intermolecular interaction with the calciums of protomer 3, explaining the observed disturbance of crystal packing. Binding of MOβDG or PE in the common site probably stabilises the whole calcium binding region including Asn59 which binds MOβDG and calcium and Asp58 which binds calcium. Both PE and PC probably bind at the calcium in CRP.

SAP rapidly aggregates in neutral solutions in the presence of calcium ions presumably due to intermolecular interactions involving the surface of the decamer with the exposed calcium binding site. This is consistent with the observation that this interaction can be inhibited by MOβDG [44] and PE (unpublished observations). Similarly they compete for the calcium site with Glu167 which is an important lattice contact in the pentamer crystals.

SAP also binds polyanions such as heparan sulphate, dermatan sulphate [7] and DNA [4] in the presence of calcium. It has been suggested that the DNA interaction involves a decapeptide around Arg120, with some resemblance to certain histone sequences and for which a helical structure was proposed [45]. However, in human SAP this region is not helical and other SAPs do not have arginine at this position. Nevertheless it does have affinity for multivalent anions, as demonstrated by the binding of phosphotungstate at this site in the heavy atom isomorphous derivative (see Table 1). There are several basic regions in SAP, for example Arg120, Arg77, His78, Lys79 and Arg57, which are on the same surface as the calcium and PE binding sites. It seems more likely that the phosphate backbone of DNA and the sulphated polysaccharides bind both at the calciums and at the basic sites, possibly on more than one subunit simultaneously. These extensive interactions probably account for the ability of SAP to displace from DNA the H1-type histones in chromatin [5]. The sequence differences in the basic regions and in the calcium binding region could explain the variable affinity for DNA shown by different pentraxins. Human CRP, for instance, only binds DNA at low, non-physiological ionic strength. PE and MOβDG both enhance the binding of DNA by SAP and compete with the interaction at high concentration [unpublished observations]. Similar effects are observed for SAP binding to immobilised PE [unpublished observations]. As we can find no evidence for a second binding site for PE or MOβDG in the present experimental conditions, these effects must be mediated through inter-subunit interactions.

Ligands for SAP, such as PE in phosphatidylethanolamine and MOβDG-like sugars [46], are common in microorganisms. In this respect SAP resembles CRP [13] and the mammalian C-type lectin, mannose-binding protein [47], which both recognise widely distributed microbial epitopes and are involved in host defence against infection. SAP could act either directly or via complement, since aggregated or complexed SAP [5,48] like mannose-binding protein [47] and CRP [13], can activate the classical complement pathway.

Proteinase-resistance of Pentraxins and the Treatment of Amyloidosis

SAP and CRP are both remarkably resistant to proteolytic degradation in the presence of calcium. In contrast, in the absence of calcium both are cleaved by some enzymes, particularly α-chymotrypsin and pronase [40,49]. Although this cleavage does not cause fragmentation of either the whole molecule or of the individual subunits under non-denaturing conditions, it does cause loss of calcium-binding activity by the pentraxins and abolishes their capacity for calcium-dependent ligand binding. It is, therefore, of interest that the major site of cleavage of SAP is between residues 144 and 145 whilst in CRP it is between residues 146–147 (pronase) or 145–146 (Nagarse protease). This is part of a loop that is held in place by calcium ligation, and which, in the calcium-free form, may be only loosely associated with the body of the protein and, therefore, susceptible to proteolysis. Most loops of SAP are held close to the body of the pentamer and this makes them less easily accessible to the active sites of proteolytic enzymes.

Resistance to proteinase digestion is likely to be an important aspect of the normal function of SAP, and may also contribute to the persistence of amyloid deposits. The SAP normally associated with the glomerular basement membrane and the surface of elastic fibre microfibrils [8,9] may protect these extracellular matrix constituents from inappropriate degradation. On the other hand, amyloid fibrils are abnormal extracellular structures which should be recognised and degraded, but which nevertheless persist in vivo. In this pathological situation the binding of SAP to amyloid fibrils may be responsible. Protection could result simply from coating by SAP, which is completely unaltered with respect to its normal circulating form [11], and which would, therefore, not be expected to trigger macrophage activation or phagocytosis. However, the proteinase resistance of SAP itself may be a significant factor. Availability of the complete high resolution structure of SAP and its ligand-binding site now offer the opportunity for direct modelling of competitive inhibitors of SAP binding and for engineering binding site homologues, either of which could be used as drugs to displace SAP from amyloid deposits in vivo. This opens up new avenues for treatment of amyloidosis, enabling the body to mobilise and degrade the fibrils which may otherwise be inappropriately protected by SAP.

Table 1 below relates to the method used in determining the three-dimensional structure of SAP:

Legend for TABLE 1

Heavy atom derivatives used for multiple isomorphous replacement and data collection statistics are shown in Table 1. Native data were collected from one crystal on a Hilger-Watts 290 4-circle diffractometer with Rsym=4.5% for 4112 independent reflections to 5.6 Å. High resolution native data were also collected on film at the Synchrotron Radiation Source at Daresbury Laboratory ($\gamma$=1.468 Å) using three crystals (R=7.7%) for 78951 unique reflections to 2.02 Å. The final merged data set comprised low resolution data from the diffractometer and high resolution data from the synchrotron. The major heavy atom sites were determined from inspection of difference Patterson functions and cross-phase difference Fouriers. A multiple isomorphous replacement (MIR) map was calculated, solvent flattened and averaged. Phases from both maps were used in cross-phase difference Fouriers to determine those minor sites related by the 5-fold axis to the major sites. All sites were initially refined with VECREF (I. J. Tickle) to eliminate spurious sites and then with PHARE. A final MIR map was calculated to 2.8 Å and the phasing analysis gave a figure of merit of 0.61. This map was solvent flattened [32], phases calculated and recombined with the MIR phases to give a combined figure of merit of 0.85. The solvent flattened map was then averaged using PSAVER (I. J. Tickle) and the envelope determined in the solvent flattening. The polypeptide of the β-sheet and helix were well defined. Derivative data were also scaled to native data collected from three crystals on a FAST area detector mounted on a CuKα microfocus tube (800 W) (Rsym=10.0% for 30996 independent reflections to 2.8 Å). Heavy atom sites were determined independently from those in Table 1 and were refined using MLPHARE. The resulting electron density map was solvent flattened and averaged using the programs supplied with O release 5.7. The map was similar to that used for the refinement. Problems in obtaining an interpretable map arose because not all substituted sites related by the non-crystallographic symmetry were present on early cross-phase difference Fouriers due to poor phasing from the derivatives available at the time. Two of the three derivatives with the highest phasing power were the last to be collected. These extra derivatives allowed minor sites related to the major sites by the 5-fold axis to be determined in the early derivatives as well as multiple occupancy in some sites previously thought to be singly occupied. For example the dominant thorium nitrate derivative formed a complex with eleven thoriurm sites comprising two octahedra, each with edges of approximately 4 Å and sharing an apex.

The direction of the 5-fold axis was determined from a self-rotation function [15], and the approximate position of the molecule on this axis was found by positioning a pentagonal prism in a low resolution MIR map. A six-dimensional search (3 rotations and 3 translations) for a best correlation in the map for a given rotational operation was performed using LOCROT (I. J. Tickle). The parameters were then refined with the density correlation programs of Bricogne [33].

One averaged subunit of the electron density map obtained from the solvent flattening was displayed in FRODO [50] on an Evans and Sutherland PS390. The sequence could be assigned from the position of the disulphide bridge and the putative calcium binding site for all residues in the sheets and helix. The resolution was extended with simulated annealing using non-crystallographic restraints in XPLOR [51] and rebuilding into electron density maps (coefficients 2Fo-Fc,Fo-Fc) calculated from phases that had been combined with the MIR phases until all residues had been inserted. The resolution was then extended to 2 Å and 10 calcium ions, 4 acetate ions and 879 water molecules were added. Least squares refinement in RESTRAIN [52] gave a crystallographic R-factor of 0.179 for all 78910 reflections in the resolution 8–2 Å. The r.m.s. deviations from stereochemical ideality are 0.017 Å for bond distances and 3.45° for bond angles. The average isotropic B values are 22.9 Å$^2$ for protein and 37.7 Å$^2$ for solvent molecules. There were no residues in the disallowed region of a Ramachandran plot [53]. The CCP4 suite of programs (SERC Daresbury) has been used for all crystallographic calculations, except the structural refinement.

Merging $R$ factor $\quad \sum_{hkl} \sum_{i=1}^{n} |I(hkl)_i - I(hkl)| \Big/ \sum_{hkl} \sum_{i=1}^{n} I(hkl)_i$ Isomorphous $R$ factor $\quad \sum_{hkl} |F_{deriv}(hkl) - F_{nat}(hkl)| \Big/ \sum_{hkl} |F_{nat}(hkl)|$ Phasing power $\quad \left[ \sum_{hkl} F_{heavy}^2(hkl) | \Big/ \sum_{hkl} e^2(hkl) \right]^{1/2}$ The following non-limiting Examples illustrate the invention.

EXAMPLE 1

Protocol for Testing for Inhibition of SAP Binding to Amyloid Fibrils

Amyloid fibrils are isolated from the organs, such as the spleen, obtained post mortem from patients with amyloidosis of AA or AL type, using the water extraction method of Pras et al [55]. This method is modified in that the initial saline homogenizations are conducted using Tris buffered saline containing 10 mM EDTA to ensure complete dissociation of all endogenous SAP [56]. The fibril-rich water extract is mixed with Tris buffered saline containing calcium chloride to bring the final salt concentration to 138 m NaCl, 10 mM Tris, 2 mM CaCl$_2$, pH 8.0, and this is then centrifuged at 1500 g for 5 minutes to sediment the fibrils. These are then resuspended in Tris saline calcium buffer, pH 8.0, at the same concentration as above (TC buffer), so as to provide a suitable suspension, for example, $A_{280}$=0.255, $A_{320}$=0.132, and this is stored at 4° C. Highly purified human SAP, isolated as described previously [31, 57] is radioiodinated with $^{125}$I, as previously described [58] to a specific activity of about 0.1 $\mu$C/$\mu$g and is diluted immediately before use to about 70 $\mu$g/ml in TC containing 4% w/v bovine serum albumin. Agents to be tested are dissolved at a concentration of about 10 mM in TC, or in 1:10 DMSO in water or TC. If they are active in inhibiting SAP binding they are tested at a range of lower concentrations to determine the minimal inhibitory dose.

For the assay itself 10 $\mu$l of labelled SAP is mixed with 50 $\mu$l of amyloid fibril suspension and 40 $\mu$l of the test substance and incubated, with mixing, for 60 minutes at room temperature. Controls include SAP alone without fibrils, SAP and fibrils without any potential inhibitor, SAP and fibrils in the presence of EDTA to prevent any binding of SAP, and SAP plus inhibitor without fibrils to control for non-specific effects, such as denaturation, induced by test substances. After the incubation the fibrils with bound SAP are separated from unbound SAP either by centrifugation at 1500 g for 5 minutes, or by filtration in the Millipore Multiscreen Assay system using 0.22 $\mu$ Durapore low protein binding multiwell filter plates. The fibrils are washed with TC containing 1% w/v BSA and the radioactive SAP bound is measured.

Typically about 75% of the activity offered is bound in the absence of any inhibitor; none is bound in the presence of

TABLE I

Structure determination of SAP

| DERIVATIVE | K$_2$PTI$_6$ | Na$_3$PO$_4$.12WO$_3$ | Th(NO$_3$)$_4$ | Th(NO$_3$)$_4$ | Ce(SO$_4$)$_2$ | K$_2$AuCl$_4$ | UO$_2$SO$_4$ | AgNO$_3$ | Na$_2$WO$_4$ |
|---|---|---|---|---|---|---|---|---|---|
| CONCENTRATION (mM) | 5.0 | 5.0 | 4.5 | 4.5 | 17.0 | 2.5 | 25.0 | 5.0 | 11.0 |
| SOAKING TIME (h) at 20° C. | 24.0 | 60.0 | 28.0 | 28.0 | 48.0 | 1.0 | 24.0 | 24.0 | 19.0 (4°C.) |
| COLLECTION DEVICE | F | F | F | F | F | F | X | I | D |
| RESOLUTION (Å) | 3.5 | 3.5 | 4.1 | 2.8 | 3.0 | 3.5 | 3.2 | 3.4 | 6.0 |
| MERGING R FACTOR | 0.084 | 6.069 | 0.062 | 0.049 | 0.101 | 0.110 | 0.045 | 0.118 | 0.075 |
| ISOMORPHOUS R FACTOR | 0.317 | 0.237 | 0.203 | 0.278 | 0.222 | 0.310 | 0.251 | 0.165 | 0.225 |
| % COMPLETE | 88.3 | 80.3 | 91.7 | 85.8 | 76.7 | 71.1 | 81.0 | 93.4 | 97.1 |
| NUMBER OF SITES | 28 | 21 | 17 | 14 | 27 | 22 | 22 | 26 | — |
| PHASING POWER | 1.00 | 1.15 | 1.43 | 2.02 (4.1–2.8Å) | 1.02 | 1.55 | 1.29 | 1.04 | — |

D, Enraf-Nonius CAD-4 diffractometer mounted on a 1500W sealed tube;
F, Enraf-Nonius FAST area-detector mounted on a Cuk$\alpha$ microfocus tube (800W);
X, Siemens Xentronics area-detector mounted on a Siemens XP18 generator;
I, MAR research imaging plate mounted on a Siemens XP18 generator.

EDTA, and in the absence of fibrils less than 5% of the activity sediments on its own.

MOβDG, at concentrations above about 2 mM in the final incubation mixture, reduces binding to background levels. An example of a typical set of results is set out in Table 2 below:

TABLE 2

Inhibition by MOβDG of SAP binding to amyloid fibrils

| AA type amyloid fibrils ($A_{280}$) | MOβDG (mM) | SAP binding (%) |
|---|---|---|
| 0.4 | 0 | 82 |
| 0.1 | 0 | 63 |
| 0.025 | 0 | 13 |
| 0.1 | 30 | 2 |
| 0.1 | 20 | 2 |
| 0.1 | 10 | 5 |
| 0.1 | 5 | 17 |
| 0.1 | 1 | 46 |

In the presence of EDTA, or in the absence of fibrils, apparent SAP binding was 1%.

EXAMPLE 2

Protection by SAP Against Digestion of Amyloid Fibrils in vitro and Abrogation of that Protection by MOβDG The method used is as follows:

Amyloid fibrils

Any type of amyloid fibril may used in the following protocol, for example, amyloid fibrils may be obtained ex vivo or Alzheimer's disease β-protein may be produced synthetically.

Alzheimer's disease β-protein, prepared as a synthetic peptide containing residues 1–40 was obtained from California Peptide Research, and was dissolved in pure water at 4 mg/ml, that is 1 mM. Some was kept at 4° C. ("fresh") and some was aged by incubation at 37° C. for 7 days. It is known that fibrils form very slowly in the cold but that "ageing" is associated with marked amyloid fibril formation, and this was confirmed in the present case by Congo red staining and by direct electron microscopy.

Methods and Results (a) β-protein solutions obtained as described above were diluted to 0.2 mg/ml in TC immediately before use. Highly purified human SAP in solution in 138 mM NaCl, 10 mM Tris, pH 8.0 (TN) was diluted in TN to 0.1 mg/ml, 0.5 mg/ml and 2.5 mg/ml Pronase from S. griseus was obtained from Boehringer Mannheim and was freshly prepared at 0.04 and 0.004 mg/ml in TC just before use.

Figure 5:
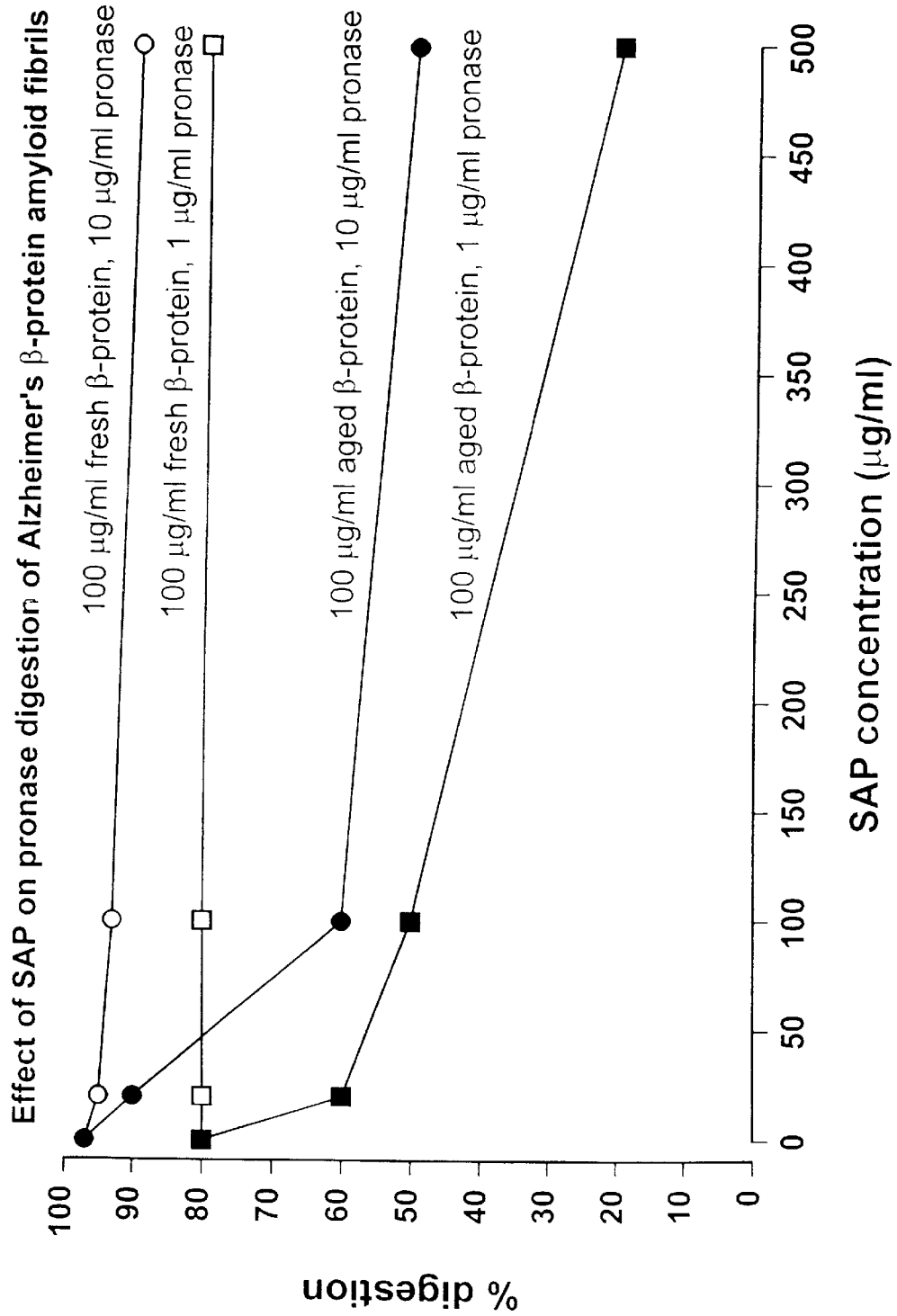
FIG. 5: Effect of SAP at concentrations of 0 to 500 μg/ml on pronase digestion of Alzheimer's β-protein amyloid fibrils.

Aliquots, 50 μl, of aged or fresh β-protein were mixed with 20 μl volumes of TN alone or SAP at the different concentrations shown in FIG. 5 and with 5 μl of 10 mM $CaCl_2$, and then incubated with shaking at 37° C. for 1 hour. TC alone or pronase in TC at 0.04 or 0.004 mg/ml were added in a volume of 25 μl and incubation continued for a further 1 hour at 37° C. Digestion was then stopped by addition of an equal volume of reducing SDS-PAGE sample buffer (20 mM Tris pH 8.0, 2 mM EDTA, 5% w/v SDS, 10% w/v 2-mercaptoethanol, 0.05% w/v bromophenol blue, 20% w/v glycerol) and boiling for 10 minutes. These samples were finally analysed in reduced SDS homogeneous 15% PAGE, stained with Brilliant blue R350. The proportion of the β-protein present in each track was estimated by scanning densitometry with reference to the no pronase control which was taken as 100%. The proportion digested was calculated by subtraction and plotted against the SAP concentration.

The results obtained are shown in FIG. 5.

(b) AA amyloid fibrils obtained ex vivo were incubated for 6 hours at 37° C. with trypsin or chymotrypsin at a substrate:enzyme ratio of 10:1 in the presence or absence of SAP and with or without MOβDG, according to the general protocol given above. The incubation mixtures were then analysed by Coomassie blue stained SDS-PAGE with quantification of the AA protein band. Intensity of this band after incubation without trypsin was taken as 100%. The results are presented in Table 3 below.

TABLE 3

Effect of SAP on proteinase digestion of AA amyloid fibrils

| Proteinase | SAP (μg/ml) | MOβDG (mM) | % AA protein remaining |
|---|---|---|---|
| — | — | — | 100 |
| Trypsin | — | — | 5 |
| Trypsin | 10 μg/ml | — | 20 |
| Trypsin | 50 μg/ml | — | 50 |
| Trypsin | 50 μg/ml | 1 mM | 5 |
| Chymotrypsin | — | — | 10 |
| Chymotrypsin | 10 μg/ml | — | 20 |
| Chymotrypsin | 50 μg/ml | — | 60 |
| Chymotrypsin | 50 μg/ml | 1 mM | 10 |

(c) In a further variant, the amyloid fibrils used (ex vivo or synthetic) may be labelled with a radioisotope, for example, radioiodine and digestion then monitored by measurement of release of trichloric acid-soluble radioactivity rather than by SDS-PAGE.

Figure 6:
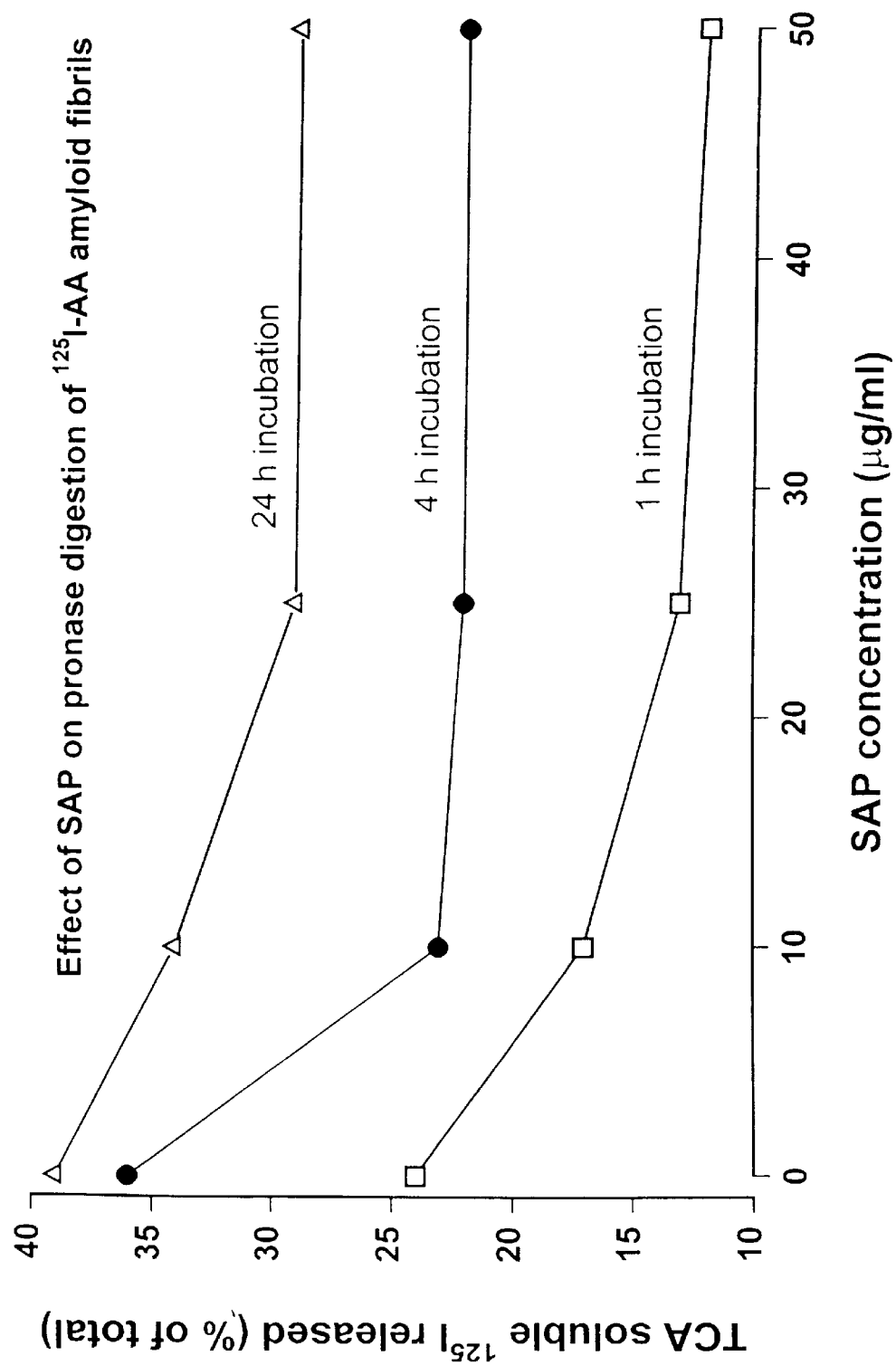
FIG. 6: Effect of SAP at concentrations of 0 to 50 μg/ml on pronase digestion of $^{125}$I-AA amyloid fibrils.
Figure 7:
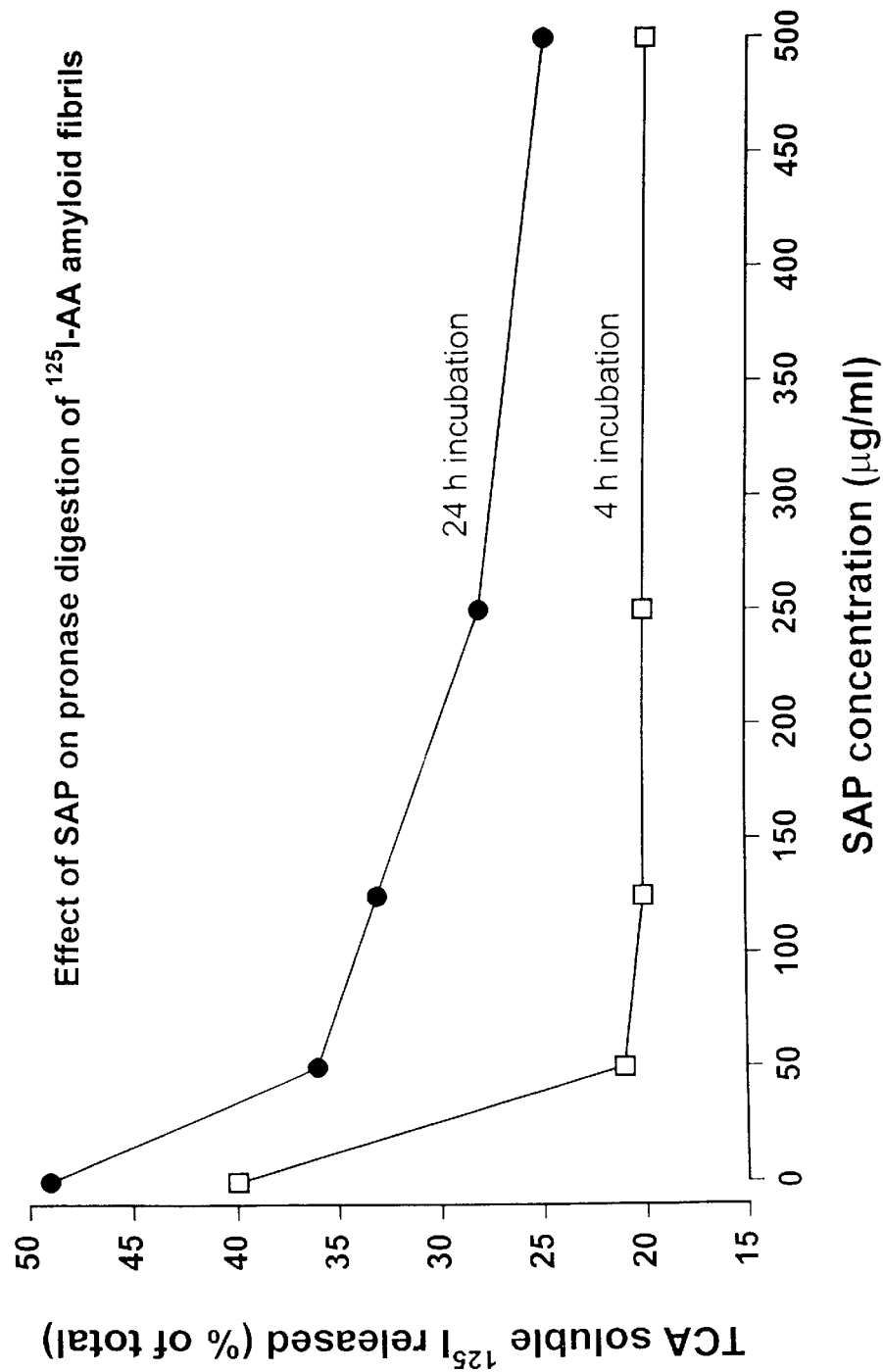
FIG. 7: Effect of SAP at concentrations of 0 to 500 μg/ml on pronase digestion cf $^{125}$I-AA amyloid fibrils.
Figure 8:
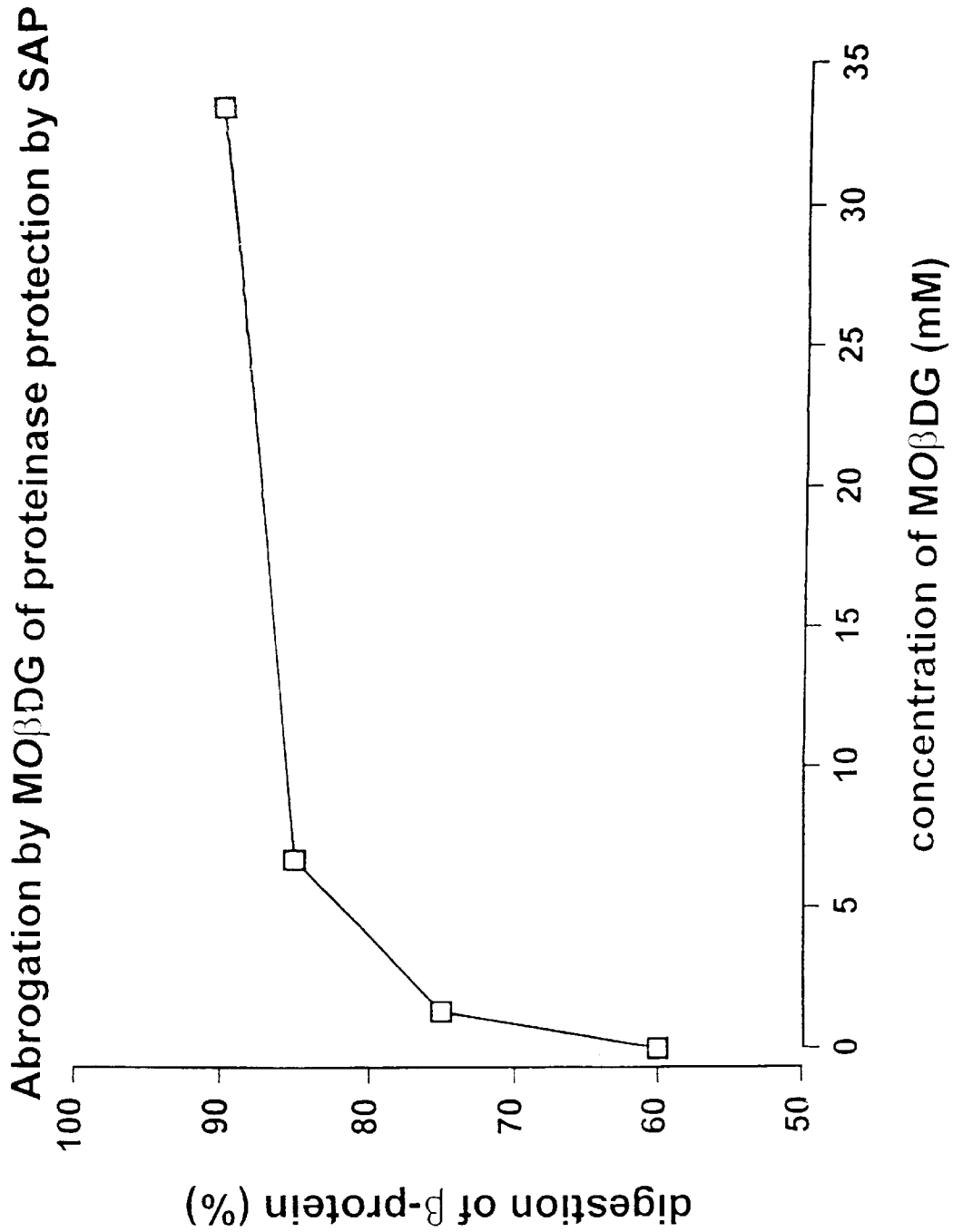
FIG. 8: Abrogation by MOβDG of proteinase protection by SAP.

AA amyloid fibrils were oxidatively labelled with $^{125}I$. The labelled fibrils were incubated with SAP and pronase following the general protocol set out above, except that the incubation was carried out for 1, 4 and 24 hours. The trichloroactic acid-soluble $^{125}I$ released was determined. FIGS. 6 and 7 show the results obtained at various SAP concentrations.

(d) Abrogation of protection by MOβDG: β-protein fibrils at 100 μg/ml were incubated for 1 hour at 37° C. with pronase at 1 μg/ml, in the presence or absence of SAP and with or without different concentrations of MOβDG. The extent of digestion of the β-protein was then estimated by SDS-PAGE analysis. The results, which demonstrate clearly the abrogation by MOβDG of the protection afforded by SAP against proteinase digestion of amyloid fibrils, are presented in Table 4 below and in FIG. 8.

TABLE 4

Abrogation by MOβDG of the protection against proteinase digestion of Alzheimer's disease β-protein fibrils conferred by serum amyloid P component

| SAP concentration (μg/ml) | MOβDG concentration (mM) | Digestion of β-protein (%) |
|---|---|---|
| 0 | 0 | 95 |
| 10 | 0 | 60 |
| 10 | 1.3 | 75 |
| 10 | 6.7 | 85 |
| 10 | 33.3 | 90 |

EXAMPLE 3

Capacity of Mice Deprived of SAP to Develop AA Amyloidosis in an Accelerated Model of Amyloidogenesis Amyloid was induced rapidly in mice by intravenous injection of an extract of amyloidotic spleen (so-called amyloid enhancing factor) together with a single profound acute phase stimulus (subcutaneous injection of silver nitrate) [59] on day 0. Group 1 had no other treatment; groups 2 and 3 received, respectively, sheep anti-mouse SAP and sheep anti-mouse C3 antibodies on day −1, day 0 and day 1. All animals were killed on day 2 and the presence of amyloid deposits sought histologically by Congo red staining.

All control animals developed appreciable splenic amyloidosis within 48 hours. In contrast all mice in which circulating SAP had been completely removed by administration of adequate doses of sheep anti-mouse SAP antiserum failed to develop any detectable amyloid deposits. A further control group which received sheep antiserum to mouse C3, an unrelated serum protein not involved in amyloidosis, almost all developed amyloid. The results are set out in Table 5 below.

TABLE 5

Effect of SAP depletion on induction of AA amyloidosis in mice

| Group | Treatment | Number of animals | Number developing amyloid | (%) |
|---|---|---|---|---|
| 1 | None | 10 | 10 | 100 |
| 2 | Anti-mouse SAP antibody | 17 | 0 | 0 |
| 3 | Anti-mouse C3 antibody | 9 | 8 | 89 |

These preliminary studies confirm that the mechanism of action of the anti-mouse SAP is indeed via SAP depletion, and show that SAP is required for amyloidogenesis. This may reflect the need for SAP to protect newly formed fibrils from proteolysis, as indicated by the work on protection of fibrils from proteolysis described above, or there may be a direct role for SAP in amyloid fibrillogenesis which has not previously been suspected. In any case the results support our in vitro results and focus attention on inhibition of SAP binding to amyloid fibrils as a most attractive target for therapeutic attack in all forms of amyloidosis. A suitable inhibitory agent will act prophylactically to prevent development of the common age-associated diseases caused by amyloid deposition, especially AD and type II (maturity onset) diabetes mellitus.

References

1. Coria, F., et al. *Lab. Invest.* 58, 454–458 (1988).
2. Pepys, M. B., Dyck, R. F., de Beer, F. C., Skinner, M. & Cohen, A. S. *Clin. exp. Immunol.* 38, 284–293 (1979).
3. Hind, C. R. K., Collins, P. M., Caspi, D., Baltz, M. L. & Pepys, M. B. *Lancet ii,* 376–378 (1984).
4. Pepys, M. B. & Butler, P. J. G. *Biochem. Biophys. Res. Comm.* 148, 308–313 (1987).
5. Butler, P. J. G., Tennent, G. A. & Pepys, M. B. *J. exp. Med.* 172, 13–18 (1990).
6. de Beer, F. C., Baltz, M. L., Holford, S., Feinstein, A. & Pepys, M. B. *J. exp. Med* 154, 1134–1149 (1981).
7. Hamazaki, H. *J. biol. Chem.* 262, 1456–1460 (1987).
8. Breathnach, S. M., et al. *Nature* 293, 652–654 (1981).
9. Dyck, R. F., et al. *J. exp. Med.* 152, 1162–1174 (1980).
10. Hind, C. R. K., et al. *J. exp. Med.* 159, 1058–1069 (1984).
11. Pepys, M. B., et al. *Proc. 41st ASMS Conference on Mass Spectrometry and Allied Topics,* San Francisco, Calif. May 30–Jun. 4, 1993 (in press).
12. Pepys, M. B., et al. *Nature* 273, 168–170 (1978).
13. Pepys, M. B. & Baltz, M. L. *Adv. Immun.* 34, 141–212 (1983).
14. Hawkins, P. N., Lavender, P. J. & Pepys, M. B. *New Engl. J. Med.* 323, 508–513 (1990).
15. Wood, S. P., et al. *J. molec. Biol.* 202, 169–173 (1988).
16. Goodford, P. J. *J. Med. Chem.* 28, 849–857 (1985).
17. Grootenhuis, P. D. J., Van Geerestein, V. J., Haasnoot, C. A. G. & Karplus, M. *Bull. Soc. Chim. Belg.* 101, 661 (1992).
18. Lawrence, M. C. & Davis, P. C. *Proteins* 12, 31–41 (1992).
19. Rotstein, S. H. & Murcko, M. A. *J. Comput. Aided Molec. Des.* 7, 23–43 (1993).
20. Blundell, T. L., Gardner, S. P., Hayes, F., Howlin, B. & Sutcliffe, M. *Eur. J. Biochem.* 172, 513–520 (1988).
21. Hawkins, P. N., et al. *Q. J. Med.* 86, 365–374 (1993).
22. Hawkins, P. N., et al. *Arthritis Rheum.* 36, 842–851 (1993).
23. Holmgren, G., et al. *Lancet* 341, 1113–1116 (1993).
24. Hawkins, P. N., et al. In: *Amyloid and Amyloidosis 1993* (Kisilevsky, R., et al., eds.), Parthenon Publishing, Pearl River, N.Y. (in press).
25. Hawkins, P. N., et al. In: *Amyloid and Amyloidosis 1993* (Kisilevsky, R., et al., eds.), Parthenon Publishing, Pearl River, N.Y. (in press).
26. Evans, S. V. *J. molec. Graphics* 11, 134–138 (1993).
27. Hutchinson, E. G. & Thornton, J. M. *Proteins* 8, 203–212 (1990).
28. Kabsch, W. & Sander, C. *Biopolymers* 22, 2577–2637 (1983).
29. Sali, A. & Blundell, T. L. *J. mol. Biol.* 212, 403–442 (1990).
30. Overington, J. P., Johnson, M. S., Sali, A. & Blundell, T. L. *Proc. roy. Soc. London ser. B* 241, 146–152 (1990).
31. Hawkins, P. N., Tennent, G. A., Woo, P. & Pepys, M. B. *Clin. exp. Immunol.* 84, 308–316 (1991).
32. Wang, B. C. *Meth. Enzymol.* 115, 90–112 (1985).
33. Bricogne, G *Acta Cryst.* A32, 832–847 (1976).
34. Sali, A., Overington, J. P., Johnson, M. S. & Blundell, T. L. *Trends Biochem. Sci.* 15, 235–240 (1990).
35. Hardman, K. D. & Ainsworth, C. F. *Biochemistry* 11, 4910–4919 (1972).
36. Einspahr, H., Parks, E. H., Suguna, K., Subramanian, E. & Suddath, F. L. *J. biol. Chem.* 261, 16518–16527 (1986).
37. Carrington, D. M., Auffret, A & Hanke, D. E. *Nature* 313, 64–67 (1985).
38. Pepys, M. B., et al. *Lancet i,* 1029–1031 (1977).
39. Tennent, G. A., et al. *Eur. J. Biochem.* 214, 91–97 (1993).
40. Kinoshita, C. M., et al. *Biochemistry* 28, 9840–9848 (1989).
41. Swanson, S. J. & Mortenson, R. F. *Molec. Immun.* 27, 679–687 (1992).
42. Liu, T. -Y. et al. *J. Protein Chem.* 6, 263–272 (1987).
43. Agrawal, A, Xu, Y., Ansardi, D., Macon, K. J. & Volanakis, J. E. *J. biol. Chem.* 267, 25352–25358 (1992).
44. Hind, C. R. K., Collins. P. M. & Pepys, M. B. *Biochim. Biophys. Acta* 802, 148–150 (1984).

45. Turnell, W. G., Satchwell, S. C. & Travers, A. A. *FEBS Lett.* 232, 263–268 (1988).
46. Hind, C. R. K, Collins, P. M., Baltz, M. L. & Pepys, M. B. *Biochem. J.* 225, 107–111 (1985).
47. Hartshorn, K. L., et al. *J. clin. Invest.* 91, 1414–1420 (1993).
48. Ying, S. C., Gewurz, A. T., Jiang, H. & Gewurz, H. *J. Immunol.* 150: 169–176 (1993).
49. Kinoshita, C. M., et al. *Protein Sci.* 1, 700–709 (1992).
50. Jones, T. A. *J. appl. Cryst.* 11, 272–282 (1978).
51. Brunger, A. T., Karplus, M. & Petsko, G. A. *Acta Cryst.* A45, 50–61 (1989).
52. Haneef, I., Moss, D. S., Stanford, M. J. & Borkakoti, N. *Acta Cryst.* A41, 426–433 (1985).
53. Ramachandran, G. N., Ramakrishnan, C. & Sasisekharan, V. *J. molec. Biol.* 1, 95–99 (1963).
54. Hardy, J. *Nature Genetics* 1, 233–234 (1992)
55. Pras, M., Schubert, M., Zucker-Frankliin, D., Rimon, A., & Franklin, E. C. *J. Clin. Invest.* 47, 924–933 (1968)
56. Nelson, S. R., Lyon, M., Gallgher, J. T., Johnson, E. A., & Pepys, M. B. *Biochem. J.* 275, 67–73 (1991)
57. de Beer, F. C. and Pepys, M. B. *J. Immunol. Methods* 50, 17–31 (1982)
58. Hawkins, P. N., Wootton, R. and Pepys, M. B. *J. Clin. Invest.* 86, 1862–1869 (1990)
59. Balz, M. L., Caspi, D., Hind, C. R. K., Feinstein, A. & Pepys, M. B. *Amyloidosis* (1990) Glenner et al., Eds., Plenum Press, New York, pp 115–121.
60. Alper, J. *Science* 264, 1399–1402 (1994)
61. Kohler & Milstein *Nature* 256, 495–497 (1975)
62. Pepys, M. B., Dash, A. C., Fielder, A. H. L. and Mirjah, D. D. *Immunology* 33, 491–499 (1977)
63. Pepys, M. B., Baltz, M., Gomer, K., Davies, A. J. S. and Doenhoff, M. *Nature* 278, 259–261 (1979)

We claim:

1. A method of screening to identify an agent for use in the treatment of amyloidosis, comprising contacting an amyloid fibril-binding serum amyloid P component and amyloid fibrils with a candidate agent, and determining the ability of the candidate agent to inhibit the binding of said serum amyloid P component to said amyloid fibrils, wherein the inhibition of amyloid fibril binding is indicative of an agent for use in the treatment of amyloidosis.

2. The method of claim 1, wherein said serum amyloid P component is a human serum amyloid P component.

3. The method of claim 1, wherein said amyloid fibrils are β-protein amyloid fibrils.

4. The method of claim 3, wherein said amyloid fibrils are human β-protein amyloid fibrils.

5. The method of claim 3, wherein said amyloid fibrils comprise a β-protein amyloid fibril peptide containing about residues 1–40 of the β-protein.

6. The method of claim 1, wherein said serum amyloid P component is a human serum amyloid P component and wherein said amyloid fibrils are human β-protein amyloid fibrils.

7. The method of claim 1, wherein either said serum amyloid P component or said amyloid fibrils are radiolabeled.

8. The method of claim 1, wherein said serum amyloid P component and said amyloid fibrils are contacted with said candidate agent in the presence of a proteinase and the ability of the candidate agent to restore proteolysis of said amyloid fibrils is determined, wherein the restoration of amyloid fibril proteolysis in the presence of said serum amyloid P component and said candidate agent is indicative of an agent for use in the treatment of amyloidosis.

9. The method of claim 8, wherein said amyloid fibrils are β-protein amyloid fibrils.

10. The method of claim 8, wherein the proteinase is trypsin, chymotrypsin or pronase.

11. The method of claim 1, wherein said candidate agent is prepared by carrying out computer-aided molecular design using the three-dimensional structure of human

SEQUENCE LISTING

```
<160> NUMBER OF SEQ ID NOS:  1

<210> SEQ ID NO 1
<211> LENGTH: 8
<212> TYPE: PRT
<213> ORGANISM: Homo sapien
<220> FEATURE:
<221> NAME/KEY: VARIANT
<222> LOCATION: (2)
<223> OTHER INFORMATION: X = ANY
<221> NAME/KEY: VARIANT
<222> LOCATION: (4)
<223> OTHER INFORMATION: X = ANY
<221> NAME/KEY: VARIANT
<222> LOCATION: (7)
<223> OTHER INFORMATION: X = ANY
<221> NAME/KEY: VARIANT
<222> LOCATION: (5)
<223> OTHER INFORMATION: X = SER OR THR

<400> SEQUENCE: 1

His Xaa Cys Xaa Xaa Trp Xaa Ser
 1               5
``` serum amyloid P component and synthesizing a molecule designed to bind to a specific binding site of human serum amyloid P component.

12. The method of claim 11, wherein said candidate agent is designed to interact with said human serum amyloid P component at about the calcium binding site identified from the three-dimensional structure of human serum amyloid P component.

13. The method of claim 11, wherein said candidate agent is designed to interact with at least one of the residues Asp58, Asn59, Glu136, Asp138 or Gln37 of human serum amyloid P component.

14. The method of claim 11, wherein said candidate agent is designed to form hydrogen bonds with the hydroxyl groups of Tyr64 and Tyr75 of human serum amyloid P component.

15. The method of claim 11, wherein said candidate agent is a non-protein molecule designed to have a three-dimensional structure similar to the three-dimensional structure of the amyloid fibril binding site of said human serum amyloid P component.

16. The method of claim 1, further comprising dispersing an identified agent that inhibits amyloid fibril binding in a pharmaceutically acceptable formulation,.

17. The method of claim 1, further comprising operatively attaching an identified agent that inhibits amyloid fibril binding to a detectable marker substance.

18. The method of claim 1, further comprising operatively attaching an identified agent that inhibits amyloid fibril binding to a pharmacologically active agent.

19. The method of claim 1, further defined as a method for identifing an agent for use in the treatment of amyloidosis connected with Alzheimer's disease.

20. A method of screening to identify an agent for use in the treatment of amnyloidosis, comprising contacting a serum amyloid P component and β-protein amyloid fibrils with a candidate agent, and determining the ability of the candidate agent to inhibit the binding of said serum amyloid P component to said β-protein amyloid fibrils, wherein the inhibition of β-protein amyloid fibril binding is indicative of an agent for use in the treatment of amyloidosis.

21. A method of screening to identify an agent for use in the treatment of amyloidosis, comprising contacting a human serum amyloid P component and human β-protein amyloid fibrils with a candidate agent, and determining the ability of the candidate agent to inhibit the binding of said human serum amyloid P component to said human β-protein amyloid fibrils, wherein the inhibition of human β-protein amyloid fibril binding is indicative of an agent for use in the treatment of amyloidosis.

22. A method of screening to identify an agent for use in the treatment of amyloidosis, comprising contacting a serum amyloid P component and amyloid fibrils with a candidate agent in the presence of a proteinase, and determining the ability of the candidate agent to restore proteolysis of said amyloid fibrils, wherein the restoration of amyloid fibril proteolysis in the presence of said serum amyloid P component and said candidate agent is indicative of an agent for use in the treatment of amyloidosis.

23. A method of screening to identify an agent for use in the treatment of amyloidosis associated with Alzheimer's disease, comprising contacting a serum amyloid P component and β-protein amyloid fibrils with a candidate agent, and determining the ability of the candidate agent to inhibit the binding of said serum amyloid P component to said β-protein amyloid fibrils, wherein the inhibition of β-protein amyloid fibril binding is indicative of an agent for use in the treatment of amyloidosis associated with Alzheimer's disease.

24. A method of screening to identify an agent for use in the treatment of amyloidosis associated with Alzheimer's disease, comprising contacting a serum amyloid P component and β-protein amyloid fibrils with a candidate agent in vitro, and determining the ability of the candidate agent to inhibit the binding of said serum amyloid P component to said β-protein amyloid fibrils, wherein the inhibition of β-protein amyloid fibril binding is indicative of an agent for use in the treatment of amyloidosis associated with Alzheimer's disease.

25. A method of screening to identify an agent for use in the treatment of amyloidosis associated with Alzheimer's disease, comprising contacting a human serum amyloid P component and human β-protein amyloid fibrils with a candidate agent in vitro, and determining the ability of the candidate agent to inhibit the binding of said human serum amyloid P component to said human β-protein amyloid fibrils, wherein the inhibition of β-protein amyloid fibril binding is indicative of an agent for use in the treatment of amyloidosis associated with Alzheimer's disease.

26. A method of screening to identify an agent for use in the treatment of amyloidosis associated with Alzheimer's disease, comprising contacting a serum amyloid P component and β-protein amyloid fibrils with a candidate agent in the presence of a proteinase in vitro, and determining the ability of the candidate agent to restore proteolysis of said β-protein amyloid fibrils, wherein the restoration of β-protein amyloid fibril proteolysis in the presence of said serum amyloid P component and said candidate agent is indicative of an agent for use in the treatment of amyloidosis associated with Alzheimer's disease.

* * * * *

UNITED STATES PATENT AND TRADEMARK OFFICE
CERTIFICATE OF CORRECTION

PATENT NO. : 6,126,918

DATED : October 3, 2000

INVENTOR(S) : Mark B. Pepys and Thomas L. Blundell

It is certified that error appears in the above-identified patent and that said Letters Patent is hereby corrected as shown below:

Title page, item [30], line 2, delete "9317120" and insert --9317120.5-- therefor.
In claim 24, column 28, lines 21-22, delete "in vitro" and insert --*in vitro*-- therefor.
In claim 25, column 28, line 32, delete "in vitro" and insert --*in vitro*-- therefor.
In claim 26, column 28, line 42, delete "in vitro" and insert --*in vitro*-- therefor.

Signed and Sealed this

Seventeenth Day of April, 2001

Attest:

NICHOLAS P. GODICI

Attesting Officer

Acting Director of the United States Patent and Trademark Office